(12) United States Patent
Moore et al.

(10) Patent No.: US 10,139,389 B2
(45) Date of Patent: Nov. 27, 2018

(54) FLUORESCENCE DETECTION OF MECHANICAL DAMAGE

(71) Applicant: The Board of Trustees of the University of Illinois, Urbana, IL (US)

(72) Inventors: Jeffrey S. Moore, Savoy, IL (US); Scott R. White, Champaign, IL (US); Nancy R. Sottos, Champaign, IL (US); Wenle Li, Urbana, IL (US); Christopher Coleman Matthews, Urbana, IL (US); Maxwell J. Robb, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 162 days.

(21) Appl. No.: 15/380,200

(22) Filed: Dec. 15, 2016

(65) Prior Publication Data

US 2017/0168037 A1   Jun. 15, 2017

Related U.S. Application Data

(60) Provisional application No. 62/267,346, filed on Dec. 15, 2015.

(51) Int. Cl.
| | | |
|---|---|---|
| *C09D 5/22* | (2006.01) | |
| *G01N 21/64* | (2006.01) | |
| *G01N 31/22* | (2006.01) | |
| *C09D 175/04* | (2006.01) | |
| *G01N 33/44* | (2006.01) | |
| *C09D 163/00* | (2006.01) | |

(52) U.S. Cl.
CPC ............. *G01N 33/442* (2013.01); *C09D 5/22* (2013.01); *C09D 163/00* (2013.01); *C09D 175/04* (2013.01); *G01N 31/22* (2013.01)

(58) Field of Classification Search
CPC ...... C09D 163/00; C09D 175/04; C09D 5/22; G01N 31/22; G01N 33/442
See application file for complete search history.

(56) References Cited

U.S. PATENT DOCUMENTS 9,409,928 B2 * 8/2016 Tang ................ B82Y 15/00
2014/0328764 A1  11/2014 Tang et al.

OTHER PUBLICATIONS

Blaiszik, B.J. et al., "Self-Healing Polymers and Composites," Annual Review Material Res., 2010,40:179-211.
Caruso, M.M. et al., "Full Recovery of Fracture Toughness Using a Nontoxic Solvent-Based Self-Healing System," Advanced Functional Materials, 2008, 18, 1898-1904.
Caruso, M.M. et al., "Robust, Double-Walled Microcapsules for Self-Healing Polymeric Materials," Applied Materials & Interfaces, vol. 2, No. 4, 1195-1199, 2010.
(Continued)

*Primary Examiner* — Jennifer Wecker
(74) *Attorney, Agent, or Firm* — Haukaas Fortius PLLC; Michael H. Haukaas

(57) ABSTRACT

An autonomic self-indicating material is provided, the material comprising a polymer composition or a composite material embedded with a microcapsule or a vascular structure comprising an aggregation-induced emission (AIE) luminogen. Upon mechanical damage to the material, the luminogen is released and aggregates, leading to fluorescence.

21 Claims, 16 Drawing Sheets

(56) References Cited

OTHER PUBLICATIONS

Davis, D.A. et al., "Force-Induced Activation of Covalent Bonds in Mechanoresponse Polymeric Materials," Nature, vol. 459, May 7, 2009, 68-72.
Mei, J. et al., "Aggregation-Induced Emission: The Whole Is More Brilliant Than the Parts," Advanced Materials, 2014, 26, 5429-5479.
Odom, S.A., et al., "Visual Indication of Mechanical Damage Using Core-Shell Microcapsules," Applied Materials & Interfaces, 2011, 3, 4547-4551.
Robb, M.J., et al., "A Robust Damage-Reporting Strategy for Polymeric Materials Enabled by Aggregation-Induced Emission," ACS Cent. Sci., 2(9):598-603, Aug. 2016.
White, S.R. et al., "Autonomic Healing of Polymer Composites," Nature, vol. 409, Feb. 15, 2001, 794-797 and 817.
Zhao, Z. et al., "Tetraphenylethene: A Versatile AIE Building Block for the Construction of Efficient Luminescent Materials for Organic Light-Emitting Diodes," Journal of Materials Chemistry, 2012, 22, 23726-23740.
Zhao, Z. et al., "Using Tetraphenylethene and Carbazole to Create Efficient Luminophores with Aggregation-Induced Emission, High Thermal Stability, and Good Hole-Transporting Property," J. Mater. Chem., 212, 22, 4527-4534.

\* cited by examiner

FLUORESCENCE DETECTION OF MECHANICAL DAMAGE

RELATED APPLICATIONS

This application claims priority under 35 U.S.C. § 119(e) to U.S. Provisional Patent Application No. 62/267,346, filed Dec. 15, 2015, which is incorporated herein by reference.

BACKGROUND

Small (micron) scale damage in polymeric materials is often difficult to detect, yet it compromises mechanical integrity and inevitably leads to failure. Strategies that enhance detection of damage are therefore important for improving safety and increasing reliability, while also reducing life cycle costs associated with regular maintenance and inspection. Moreover, systems that respond autonomously to self-report damage are appealing because no human intervention is required.

The development of self-reporting materials enables autonomous damage detection for improved safety and reliability of critical engineering components. For example, incorporation of mechanically sensitive molecules in polymeric materials through covalent or non-covalent modification facilitates color changes in response to macroscopic deformation.

Enhanced damage visibility in polymer composites has been achieved using a fluorescent dye contained within embedded hollow fibers. However, this method suffers from the absence of a "turn-on" mechanism, precluding its utility in transparent materials.

Fluorescence detection provides significantly enhanced sensitivity over absorption-based colorimetric methods. Conventional fluorophores are usually flat disc-like aromatic molecules with high planarity and rigidity which result in efficient light emission. However, typical fluorophores also exhibit diminished emission with increasing concentration. These molecules experience strong molecular interactions and thus suffer from a severe aggregation-caused quenching (ACQ) effect. Previous techniques to tackle the ACQ problem have focused on preventing aggregation but have resulted in limited success.

Visualization of damage has also been accomplished using microcapsules containing a conjugated monomer in combination with an embedded polymerization catalyst as well as pH-sensitive dyes that change color upon reaction with an auxiliary compound or with certain functional groups present in the polymer matrix. Chemical activation of an embedded fluorogenic molecule and formation of a charge-transfer complex using a dual capsule system has also been described.

Nevertheless, the foregoing current damage detection methods generally rely on chemical reactions to elicit a response and are highly material-dependent or complicated by multiple components. The solution presented in this disclosure provides a damage detection approach which does not rely on chemical reactions but instead on the unique feature of aggregation-induced emission (AIE) luminogens, which have been used for other applications in areas such as solid state optoelectronic devices and rewritable media for optical data storage.

SUMMARY

Microscopic damage inevitably leads to failure in polymers and composite materials, but it is difficult to detect without the aid of specialized equipment. The ability to enhance the detection of small-scale damage prior to catastrophic material failure is critical for improving the safety and reliability of critical engineering components, while simultaneously reducing life cycle costs associated with regular maintenance and inspection. Systems that respond autonomously to damage are particularly appealing, as they require no human intervention to reveal locations of diminished mechanical integrity.

Here, we demonstrate a simple, robust, and sensitive fluorescence-based approach for autonomous detection of damage in polymeric materials and composites that employs a physical change of state to indicate damage enabled by aggregation-induced emission (AIE). AIE luminogens are molecules that possess vibrational and/or rotational modes capable of relaxing the energy of absorbed photons non-radiatively when dissolved in solution. Whereas, aggregation restricts this intramolecular motion and promotes efficient photoluminescence. This simple, yet powerful "turn-on" system relies on a single active component and the general mechanism delivers outstanding performance in a wide variety of materials with diverse chemical and mechanical properties.

With this detection scheme, mechanical damage triggers rapid generation of a local fluorescence signal that is easily visualized under UV light and provides excellent contrast between intact and damaged regions of a material (FIG. 5). The general indication mechanism enables the unaided detection of damage less than 2 μm in size in a wide variety of materials prepared using diverse fabrication methods. Microencapsulation, for example, offers a robust and versatile platform where mechanical rupture triggers the release of a payload.

This system autonomously indicates, for example, the location of mechanical damage in polymer and composite materials by visualization of a fluorescence signal. Microcapsules containing a solution of a compound that becomes fluorescent upon aggregation are embedded in a polymer coating or composite material. When the material is damaged, the microcapsules release their payload and subsequent aggregation of the core material causes the damaged location to become fluorescent.

Accordingly, this disclosure provides an apparatus for an autonomous self-indicating material comprising a plurality of microcapsules encapsulating a non-emissive solution, the solution comprising an aggregation-induced emission (AIE) fluorophore and a solvent, wherein when the material is impacted by a sufficient force to damage it, one or more microcapsules are ruptured, the non-emissive solution is released from ruptured microcapsules, the fluorophore aggregates at or near the point of rupture, and the aggregated fluorophore is emissive to autonomically self-indicate a location where damage has occurred in the material.

Additionally, this disclosure provides a method for detecting damage to an autonomous self-indicating material, the method comprising:

a) irradiating an autonomous self-indicating material with ultraviolet light, wherein the material comprises a plurality of microcapsules encapsulating a non-emissive solution comprising an aggregation-induced emission (AIE) fluorophore and a solvent, wherein when the material is impacted by a sufficient force to damage it, one or more microcapsules are ruptured, the non-emissive solution is released from ruptured microcapsules, the fluorophore aggregates at or near the point of rupture, and the aggregated fluorophore is emissive to autonomically self-indicate a location where damage has occurred in the material; and b) determining if a fluorescent signal is emitted by the fluorophore, wherein the absence of the fluorescent signal indicates that there is no damage to the material and the presence of the fluorescent signal autonomically self-indicates the location of damage to the material.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

(b) Scratched epoxy coatings containing 10 wt % TPE microcapsules (diameter of 57±8 μm) with core solution concentrations of 0.5 wt % (13 mM) or 1.0 wt % (26 mM) TPE in hexyl acetate.

Figure 13:
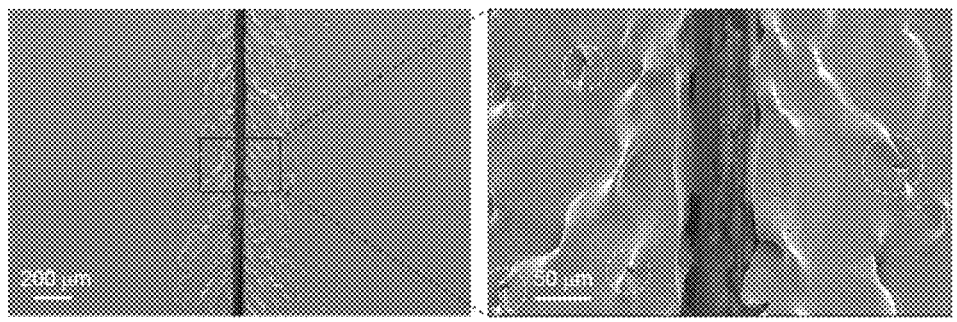

FIG. 13. SEM images of epoxy coating containing 10 wt % TPE microcapsules showing ruptured microcapsules at the surface of the sheared region adjacent to the primary scratch damage (marked with white dashed circles).

Figures 14A, 14B:
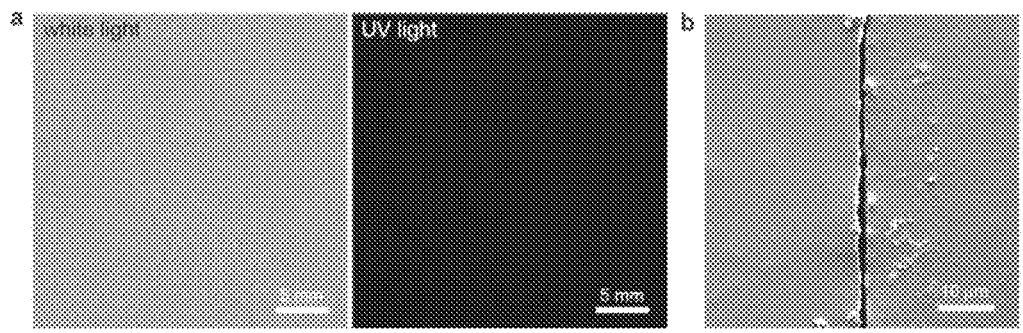
Figures 15A, 15B, 15C, 15D:
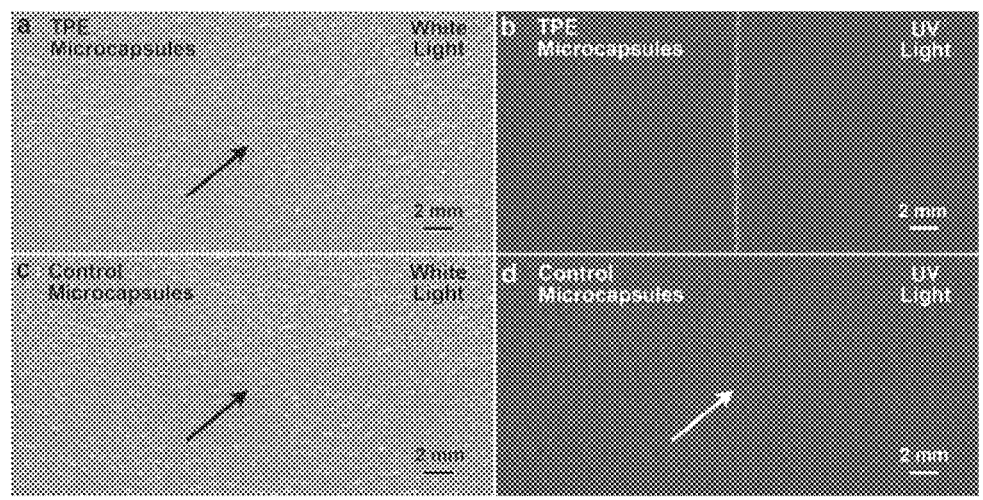

FIG. 14A-14B. (a) Photographs under illumination with white light and UV light of a polyurethane coating containing 10 wt % control microcapsules after being scratched with a razor blade; (b) SEM image of the same polyurethane coating showing the scratch damage. The scratch damage is undetectable without equipment-aided visualization.

FIG. 15A-15D. Photographs of polyurethane coatings containing 10 wt % TPE microcapsules or control microcapsules under illumination with white light or UV light after being scratched with a razor blade. (a) TPE microcapsules under white light; (b) TPE microcapsules under 365 nm UV light; (c) control microcapsules under white light; (d) control microcapsules under 365 nm UV light. The location of the scratch is identified with an arrow in images (a), (c), and (d).

Figure 16:
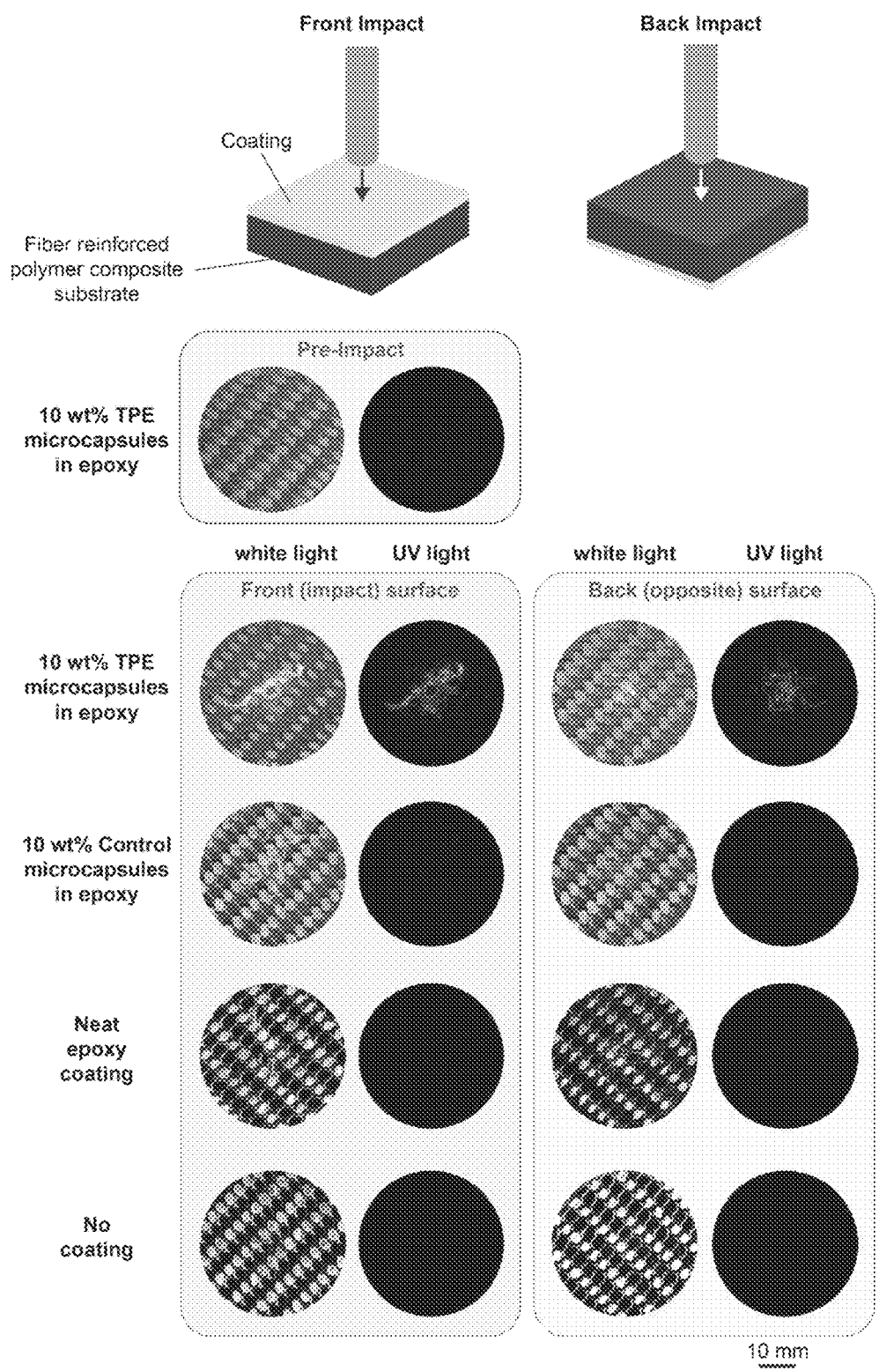
Figures 17A, 17B, 17C, 17D:
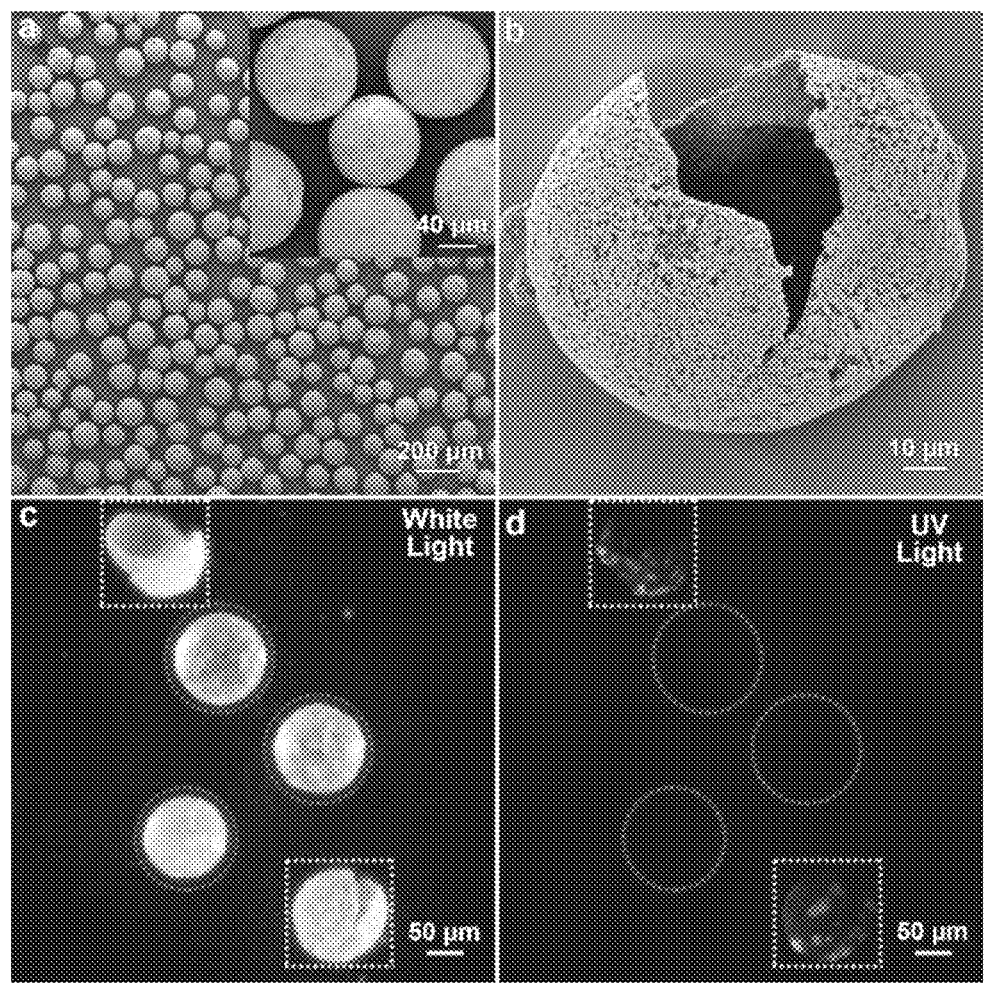
Figures 18A, 18B, 18C, 18D, 18E:
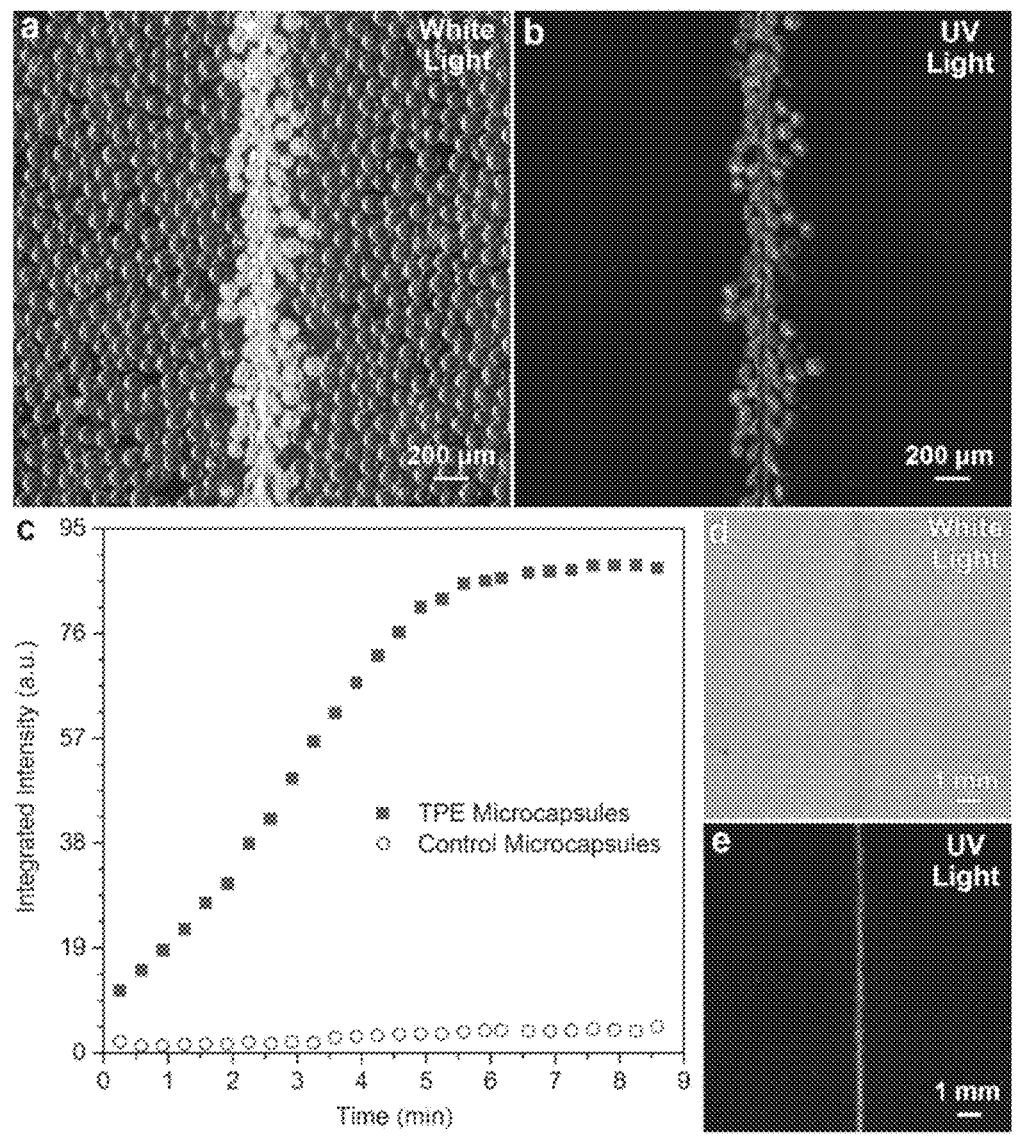

FIG. 16. Photographs of carbon fiber reinforced composites with various coatings after impact damage under white light and UV light. The schematic above illustrates the two different impact damage procedures.

FIG. 17A-17D. Characterization of TPE microcapsules and damage-induced fluorescence. SEM images of (a) as-prepared and (b) ruptured TPE microcapsules. Stereomicrographs of TPE microcapsules under (c) white light and (d) UV light demonstrate damage-induced fluorescence. Under UV light, intact microcapsules are undetectable while ruptured capsules generate a distinct fluorescence signal.

FIG. 18A-18E. Analysis of transparent epoxy coatings containing TPE microcapsules after being scratched with a razor blade. (a,b) Stereomicrographs recorded under white light and 365 nm UV light demonstrate damage-induced fluorescence in the scratched region of the coating. (c) Time-dependent fluorescence microscopy measurements illustrate rapid development of the fluorescence signal after damage to the coating containing TPE microcapsules while the control coating exhibits negligible change in fluorescence. (d,e) Photographs of the damaged epoxy coating containing TPE microcapsules under white light and UV light highlight the enhanced visual indication of damage with fluorescence detection.

DETAILED DESCRIPTION

Combination of a AIE luminogen with a microcapsule delivery approach has proved to be a robust and versatile platform for autonomous indication of damage in a wide range of materials using straightforward visual fluorescence detection.

Figure 1:
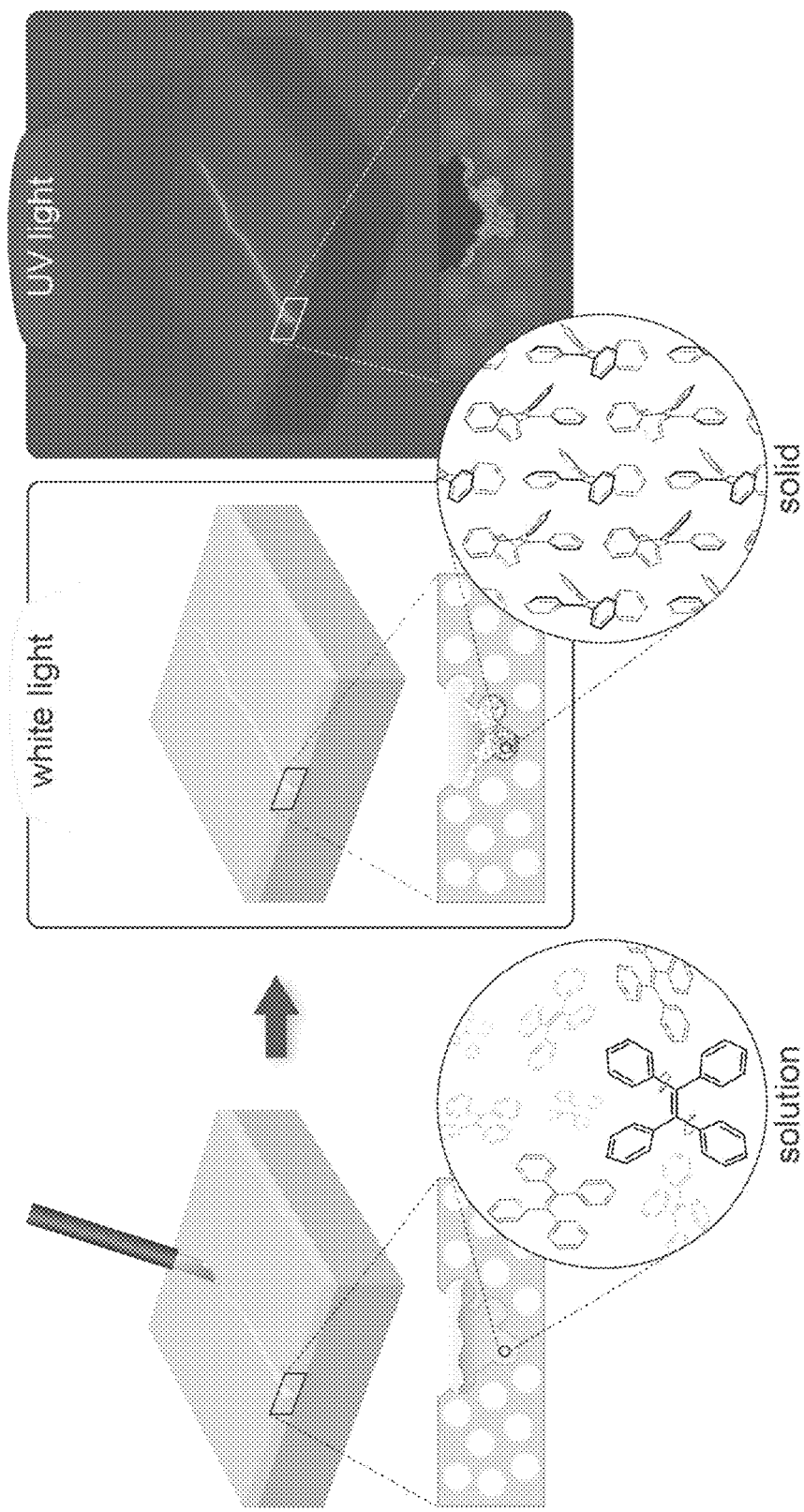
FIG. 1. Schematic of the autonomous damage detection system. Core-shell microcapsules containing a dilute solution of AIE luminogen are embedded in a polymeric material. Mechanical damage causes microcapsules to rupture and release their liquid payload. Subsequent evaporation of the solvent causes solid AIE luminogen to deposit in the damaged region, which fluoresces under UV light. The core solutions contained within intact microcapsules remain nonemissive, providing excellent contrast between damaged and undamaged regions of the material.

We developed a turn-on detection system in which core-shell microcapsules release a solution of an AIE luminogen upon mechanical damage resulting in local fluorescence indication after solvent evaporation. The damage detection system is illustrated schematically in FIG. 1. Core-shell microcapsules containing a dilute, non-fluorescent solution of AIE luminogen are embedded in a polymeric material. Following mechanical damage, rupture of the microcapsules results in the release of the encapsulated solution in the region of damage. Subsequent spontaneous evaporation of the solvent causes aggregation of the AIE luminogen and generation of fluorescence that is visualized under an appropriate excitation light source. This approach provides a number of advantages for damage detection. For example, this simple, one-component design does not rely on inter-molecular interactions and is anticipated to perform similarly in a variety of materials. Furthermore, advancements in encapsulation chemistry, the ready availability of diverse AIE luminogens, and the facile incorporation of microcapsules into existing materials formulations make this technology highly accessible.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit. For example, one or more substituents on a phenyl ring refers to one to five, or one to four, for example if the phenyl ring is disubstituted.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements. When values are expressed as approximations, by use of the antecedent "about," it will be understood that the particular value without the modifier "about" also forms a further aspect.

The terms "about" and "approximately" are used interchangeably. Both terms can refer to a variation of ±5%, ±10%, ±20%, or ±25% of the value specified. For example, "about 50" percent can in some embodiments carry a variation from 45 to 55 percent, or as otherwise defined by a particular claim. For integer ranges, the term "about" can include one or two integers greater than and/or less than a recited integer at each end of the range. Unless indicated otherwise herein, the terms "about" and "approximately" are intended to include values, e.g., weight percentages, proximate to the recited range that are equivalent in terms of the functionality of the individual ingredient, composition, or embodiment. The terms "about" and "approximately" can also modify the end-points of a recited range as discussed above in this paragraph.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. It is therefore understood that each unit between two particular units are also disclosed. For example, if 10 to 15 is disclosed, then 11, 12, 13, and 14 are also disclosed, individually, and as part of a range. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents. It will be further understood that the endpoints of each of the ranges are significant both in relation to the other endpoint, and independently of the other endpoint.

The term "substantially" as used herein, is a broad term and is used in its ordinary sense, including, without limitation, being largely but not necessarily wholly that which is specified.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to bring about a recited effect, such as an amount necessary to form products in a reaction mixture. Determination of an effective amount is typically within the capacity of persons skilled in the art, especially in light of the detailed disclosure provided herein. The term "effective amount" is intended to include an amount of a compound or reagent described herein, or an amount of a combination of compounds or reagents described herein, e.g., that is effective to form products in a reaction mixture. Thus, an "effective amount" generally means an amount that provides the desired effect.

A "sufficient" amount refers to an amount sufficient to bring about a recited effect, such as an amount of damage inflicted to a coating that is necessary to rupture one or more microcapsules, thereby releasing the agents contained therein. Thus, a "sufficient" amount generally means an amount that provides the desired effect.

"Aggregation-induced emission" or in short "AIE" means the fluorescence/phosphorescence is turned on upon aggregation formation or in the solid state. When molecularly dissolved, the material with this property is nonemissive. However, the emission is turned on when the intramolecular rotation is restricted. Examples of AIE fluorophores include, but are not limited to, for example, those described by U.S. Patent Publication No. 2014/0328764; Luo et. al., *Chem Commun.* 2001, 1740; Hong et. al., *Chem Commun.* 20096, 4332; Hong et. al., *Chem. Soc. Rev.,* 2011, 40, 5361; and Zhang et. al., *Anal. Chem,* 2015, 87, 1351-1357. Any suitable and effective aggregation-induced emission fluorophore can be used in the embodiments described herein. For example, in one embodiment, the AIE fluorophore is 1,1,2,2-tetraphenylethylene.

The term "polymer" means a macromolecule, composed of many repeated subunits, which embodies a characteristic of high molecular mass and attendant properties. The term "prepolymer" means a precursor macromolecule or molecule containing intermediates or reactive functional groups that can undergo further reaction to form a polymer. In some embodiments, the term "polymer" refers to a substance containing 100 or more repeating units. A polymer can include soluble and/or fusible moieties having long chains of repeat units, and can optionally include insoluble and infusible networks. In some embodiments, the term "prepolymer" refers to a substance containing less than 100 repeat units and that can undergo further reaction to form a polymer.

The term "capsule" means a closed object having a capsule wall enclosing an interior volume that may contain a solid, liquid, gas, or combinations thereof, and having an aspect ratio of 1:1 to 1:10. The aspect ratio of an object is the ratio of the shortest axis to the longest axis, where these axes need not be perpendicular. A capsule may have any shape that falls within this aspect ratio, such as a sphere, a toroid, or an irregular amoeboid shape. The surface of a capsule may have any texture, for example rough or smooth.

The phrase "autonomic self-indicating material" refers to automatically (without human or electronic control intervention) stopping, starting and adapting operation of the self-indicating material depending on environmental, physical, or chemical stimuli. The objective of the self-indicating material is to indicate the environmentally or physically damaged region of the material without any human or machine involvement. For example, when environmental, physical, or chemical stimuli damage the material so as to rupture the described microcapsules contained therein or degrade the shell-wall of the microcapsules, autonomic indication of the damaged region can be achieved. Similarly, the material can also be designed to autonomically heal the damaged region and autonomically indicate that the damaged region has been healed.

Embodiments of the Invention

The materials and methods now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements.

Likewise, many modifications and other embodiments of the materials and methods described herein will come to mind to one of skill in the art to which the invention pertains having the benefit of the teachings presented in the foregoing descriptions and the associated drawings.

EPON 813™ (Hexion)

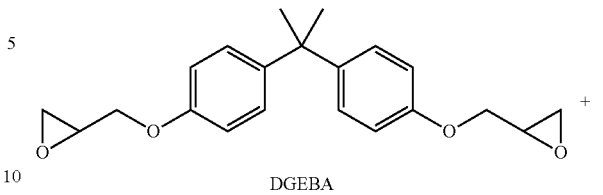

DGEBA

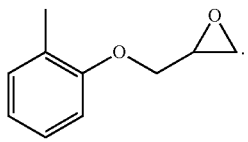

26% o-Cresyl Glycidyl Ether

Homo-polymerized DGEBA

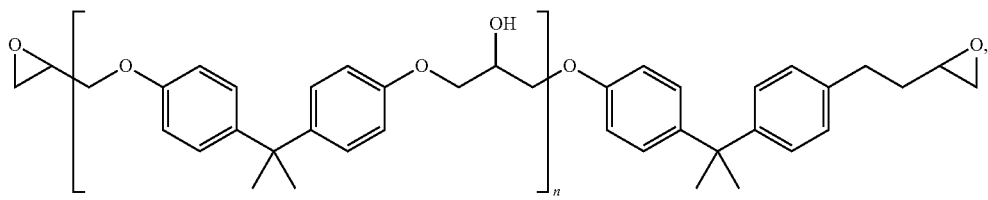

In various embodiments, an autonomous self-indicating material comprises a plurality of microcapsules encapsulating a non-emissive solution, the solution comprising an aggregation-induced emission (AIE) luminogen and a solvent;

wherein when the material is impacted by a sufficient force to damage it, one or more microcapsules are ruptured, the non-emissive solution is released from ruptured microcapsules, the luminogen aggregates at or near the point of rupture, and the aggregated luminogen is emissive to autonomically self-indicate a location where damage has occurred in the material.

In another embodiment, the self-indicating material comprises a polymer. The polymer can comprise an epoxy resin, a polyurethane, bisphenol A epoxy resin, bisphenol F epoxy resin, novolac epoxy resin, an aliphatic epoxy resin, a cycloaliphatic epoxy resin, a glycidylamine epoxy resin, a water-based epoxy resin, a bisphenol A diglycidyl ether (DGEBA) based resin, polyurethane, polydimethylsiloxane, polyacrylic acid, polystyrene, or a combination thereof.

In some other embodiments, the epoxy resin composition comprises diglycidyl ether of bisphenol F (DGEBF). In a certain embodiment, the epoxy resin composition comprises an epoxy resin diluted with a low viscosity reactive diluent. In some embodiments, the low viscosity reactive diluent comprises ethyl hexyl glycidyl ether, trimethylol propane triglycidyl ether, phenyl glycidyl ether, or cyclohexane dimethanol diglycidyl ether. In one embodiment, the low viscosity reactive diluent comprises o-cresyl glycidyl ether (o-CGE). In one particular embodiment, the bisphenol-A epoxy resin composition comprises EPON 813™ (HEXION) liquid epoxy resin (low viscosity resin with crystallization resistance).

where n denotes the number of polymerized subunits and can number in the tens of thousands or more. In some embodiments, n is in the range from 0 to 25 or about 1 to about 25, e.g., 5-20.

As with other classes of thermoset polymer materials, the epoxy resin compositions can be formulated by blending different grades of epoxy resin, and/or adding additives, plasticizers, or fillers to achieve desired processing and/or final properties, or to reduce cost. Curing can be achieved by reacting an epoxy with itself (homo-polymerization) or by forming a co-polymer with polyfunctional curatives or hardeners. In principle, any molecule containing a reactive hydrogen may react with the epoxide groups of the epoxy resin. Common classes of hardeners for epoxy resins include amines, acids, acid anhydrides, phenols, alcohols and thiols. Relative reactivity (lowest first) is approximately in the order: phenol<anhydride<aromatic amine<cycloaliphatic amine<aliphatic amine<thiol. The epoxy curing reaction may be accelerated by addition of small quantities of accelerators. Tertiary amines, carboxylic acids and alcohols (especially phenols) are effective accelerators. Bisphenol A is a highly effective and widely used accelerator.

In another embodiment of the invention, the polymeric material comprises an epoxy resin composition and a catalyst, such as a photo-polymerization catalyst. In certain embodiments, the photo-polymerization catalyst comprises a cationic photoinitiator. In some embodiments, the photo-polymerization catalyst comprises IRGACURE® 250 (Iodonium, (4-methylphenyl)[4-(2-methylpropyl) phenyl]-, hexafluorophosphate) (BASF), THP (triarylsulfonium hexafluorophosphate salts) (SIGMA-ALDRICH), THA (triarylsulfonium hexafluoroantimonate salts) (SIGMA-ALDRICH), or DARACUR® 1173 (2-hydroxy-2-methyl-1-phenylpropan-1-one (CIBA).

In other embodiments, the microcapsules comprise about 1 weight percent to about 30 weight percent of the total weight of the material, about 5 weight percent to about 25 weight percent of the total weight of the material, or about 10 weight percent to about 20 weight percent of the total weight of the material.

In additional embodiments, the solvent comprises an (alkyl)acetate, an alcohol, an ether, an alkane, a ketone, a nitrile, water, an aromatic hydrocarbon, a protic solvent, an aprotic solvent, or a combination thereof.

For example, the capsules may contain one or more solvents, stabilizers, antioxidants, flame retardants, plasticizers, colorants and dyes, fragrances, or adhesion promoters. Examples of capsules that include a solvent are disclosed, for example, in U.S. Pat. No. 9,108,364 (Caruso et al.). The capsules may include an aprotic solvent, a protic solvent, or a mixture of these. Examples of aprotic solvents include alkanes and hydrocarbons, such as hexane, cyclohexane, cyclopentane, and heptane; aromatic hydrocarbons, such as toluene and xylenes; halogenated hydrocarbons, such as dichloromethane; halogenated aromatic hydrocarbons, such as chlorobenzene and dichlorobenzene; substituted aromatic solvents, such as nitrobenzene; ethers, such as tetrahydrofuran (THF) and dioxane; ketones, such as acetone and methyl ethyl ketone; esters, such as ethyl acetate, hexyl acetate, ethyl phenylacetate (EPA) and phenylacetate (PA); tertiary amides, such as dimethyl acetamide (DMA), dimethyl formamide (DMF) and N-methyl pyrrolidine (NMP); nitriles, such as acetonitrile; and sulfoxides, such as dimethyl sulfoxide (DMSO). Examples of protic solvents include water; alcohols, such as ethanol, isopropanol, butanol, cyclohexanol, and glycols; and primary and secondary amides, such as acetamide and formamide.

In various embodiments, the solution comprises the luminogen at about 0.1 weight percent to about 20 weight percent, about 1 weight percent to about 15 weight percent, or about 5 weight percent to about 10 weight percent.

In various embodiments, the microcapsules have a thermal stability up to about 400° C., up to about 350° C., up to about 300° C., up to about 250° C., up to about 200° C., up to about 150° C., or up to about 100° C.

In additional embodiments, the diameter of the microcapsules is about 200 nm to about 500 μm, 300 nm to about 300 μm, about 1000 nm to about 250 μm, about 10 μm to about 200 μm, or about 25 μm to about 150 μm. In other embodiments, the microcapsules have a shell-wall thickness of about 10 nm to about 50 μm, about 10 nm to about 800 nm, about 10 nm to about 500 nm, about 75 nm to about 700 nm, about 150 nm to about 600 nm, or about 100 nm to about 500 nm.

In yet other embodiments, the microcapsules comprise a double-walled mixture of polyurethane and poly(ureaformaldehyde), or the microcapsules comprise a single-wall of polyurethane or poly(ureaformaldehyde). The microcapsules can be mixed in an epoxy resin film. In some embodiments of the invention, the epoxy resin film comprises zinc-pigmented epoxies, water-based epoxies, or DGEBA-based resins. In certain embodiments, the epoxy resin film comprises EPI-REZ™ 6520-WH-53 resin (HEXION) and EPIKURE™ 6870-W-53 (HEXION) curing agent.

Capsules may be made by a variety of techniques, and from a variety of materials. Examples of materials from which the capsule shell materials may be made, and the techniques for making capsules include: poly(urea-formaldehyde), polyurethane, and polyurea formed by interfacial polymerization; polystyrene, polydimethylsiloxane, and poly(phthalaldehyde) formed by solvent evaporation; and each of the previously mentioned capsules prepared by a microfluidic approach. In some embodiments, capsules can be prepared from the following materials by the following corresponding techniques: polyurethane, formed by the reaction of isocyanates with a diol or triol; urea-formaldehyde (UF), formed by in situ polymerization; gelatin, formed by complex coacervation; polystyrene, formed by complex coacervation; polyurea, formed by the reaction of isocyanates with a diamine or a triamine, depending on the degree of crosslinking and brittleness desired; polystyrene or polydivinylbenzene formed by addition polymerization; and polyamide, formed by the use of a suitable acid chloride and a water soluble triamine. For capsules having an average diameter less than about 10 micrometers, the capsule formation may include forming a microemulsion containing the capsule starting materials and forming microcapsules from this microemulsion.

In additional embodiments, a substrate comprises a coating wherein the substrate comprises steel, aluminum, iron, zinc, copper, titanium, carbon, silica, a ceramic, cellulose, glass, a fiber, a polymer, or a combination thereof. In further embodiments, the thickness of the coating is about 5 μm to about 10000 μm, about 10 μm to about 1000 μm, about 20 μm to about 500 μm, or about 50 μm to about 500 μm.

The substrate can be anything designed to carry a load, such as a structural or non-structural (e.g., elastomer) substrate. A structural substrate is one that carries the load with minimal deflection. Structural substrates can additionally include metal, non-metal, and polymeric materials. In certain embodiments, the structural substrate comprises a polymeric structural composite (PMC). PMCs are composed of high strength/stiffness fibers, held together by a polymer matrix material. Common examples include a carbon fiber composite, glass fiber, an epoxy resin, or a combination thereof. In one embodiment, the PMC comprises a combination of an epoxy resin with glass fiber or carbon fiber. The epoxy can be vacuum infused into the glass fiber or the carbon fiber to create a glass or carbon fiber reinforced epoxy composite. In other embodiments, the structural substrate is steel.

In various embodiments, the luminogen is 1,1,2,2-tetraphenylethylene (TPE), fluorescein, hexaphenylsilole (HPS), 10,10',11,11'-tetrahydro-5,5'-bidibenzo[a,d][7]annulenylidene (THBA), 9-(diphenylmethylene)-9 H-fluorene (DPMF), or 9,10-Bis(p-dimethylaminostyryl)anthracene.

In other various embodiments, an autonomous self-indicating composite material comprises a vessel containing a non-emissive solution comprising an aggregation-induced emission (AIE) luminogen and a solvent; a mixture of a polymer and a plurality of vessels; and a substrate comprising a coating of the mixture; wherein when the composite is impacted by a sufficient force to damage it, one or more vessels are ruptured, the non-emissive solution is released from each ruptured vessel, the luminogen aggregates at or near the point of rupture, and the aggregated luminogen is emissive to autonomically self-indicate a location where damage has occurred in the composite material.

In various additional embodiments, the vessel is a substantially spheroid microcapsule encapsulating the solution, or the vessel has a microvascular structure comprising a hollow network of channels or fibers or capillaries, or a combination thereof, wherein the vessel is partially or substantially filled with the solution.

Other embodiments of the disclosure include a method for preparing the autonomous self-indicating material, the method comprising:

a) dissolving a luminogen in a solvent to form a non-emissive solution; b) preparing microcapsules and encapsulating the non-emissive solution into the microcapsules; c) mixing an epoxy resin or a polyurethane with the microcapsules to form the material; and; d) coating the material onto a substrate.

Additional embodiments include a method for detecting damage to an autonomous self-indicating material, the method comprising:

a) irradiating an autonomous self-indicating material with ultraviolet light, wherein the material comprises a plurality of microcapsules encapsulating a non-emissive solution comprising an aggregation-induced emission (AIE) luminogen and a solvent;

wherein when the material is impacted by a sufficient force to damage it, one or more microcapsules are ruptured, the non-emissive solution is released from ruptured microcapsules, the luminogen aggregates at or near the point of rupture, and the aggregated luminogen is emissive to autonomically self-indicate a location where damage has occurred in the material; and b) determining if a fluorescent signal is emitted by the luminogen;

wherein the absence of the fluorescent signal indicates that there is no damage to the material and the presence of the fluorescent signal autonomically self-indicates the location of damage to the material. In further embodiments, the composite is irradiated with ultraviolet light, for example, light of about 365 nm, or any other suitable and effective wavelength.

In various embodiments, the microcapsules are ruptured, the solvent is substantially removed from the point of rupture by evaporation, diffusion, absorption, adsorption, or a combination thereof. In other embodiments, the solvent is substantially removed in less than about 24 hours, less than about 1 hour, less than about 30 minutes, less than 15 minutes, less than 10 minutes, less than 5 minutes, or less than 1 minute.

Various embodiments of the invention include a method for detecting damage to the autonomous self-indicating material of claim 1 comprising: a) irradiating the material with ultraviolet light; and b) determining if a fluorescent signal is emitted by the organic luminogen; wherein the absence of the fluorescent signal indicates that there is no damage to the material and the presence of the fluorescent signal autonomically self-indicates the location of damage to the material.

The current disclosure provides a system in which core—shell microcapsules containing an aggregation-induced emission (AIE) fluorophore solution are embedded in a polymeric coating or structural composite material. Initially, the dilute solution of an AIE fluorophore contained within the intact microcapsules would be non-emissive; however, upon rupture of the microcapsules and removal of the solvent by evaporation or other spontaneous processes, aggregation of the fluorophore would cause the damaged area to become fluorescently labeled.

This approach provides a number of immediate advantages over existing technologies. Our one-component system is general and does not rely on any specific interactions with the substrate or matrix to elicit a fluorescence response and is anticipated to function similarly in a variety of host materials. The non-specific action of fluorescence indication enables damage detection in a wide range of materials having diverse chemical and mechanical properties. The microcapsules can be colorless and do not influence the color of the matrix material. Rapid development of a fluorescence signal can occur immediately after mechanical damage. Maximum fluorescence signal is typically achieved in less than 10 minutes. Regions of mechanical damage remain permanently fluorescent (provided, for example, no chemical or physical treatment removes the luminogen), allowing a wide timeframe for examination in the field.

A very bright fluorescence response is achieved using microcapsules containing low concentrations of active material in the core of the microcapsules (e.g., approximately 1 weight %). Suitable and effective low concentrations of active material in the core of the microcapsules for damage indication include about 0.05 wt % to about 2 wt %. Typical low concentrations that can be effective include about 0.05 wt %, 0.1 wt %, 0.5 wt %, 1 wt %, 1.5 wt %, 2 wt %, and 2.5 wt %, and ranges from one to any other of these recited values. The upper limit of the concentration is the solubility limit of a specific fluorophore or luminogen in the specific solvent used in the core; the lower limit is a concentration that provides sufficient indicating contract by one or more methods of detection described herein. In certain specific embodiments, the active material is TPE. When other types of fluorophore or luminogen are employed, the concentration of active material may be increased or decreased by plus or minus about 10%, plus or minus about 25%, or plus or minus about 50%. The system does not require, and typically does not use, any metals or other expensive components. In addition, a very high contrast is achieved between damaged and undamaged regions of a specimen. Intact microcapsules (located in undamaged regions of the material) are completely non-fluorescent.

The damage indication does not occur until an area of the substrate is sufficiently damaged so as to break open the outer shell wall of the microcapsules or the vascular structure. The outer shell (e.g., polymer shell-wall) provides protection (e.g., thermal, chemical, and mechanical stability) from unintended rupturing. Accordingly, the outer shell can be a single wall or a multi-wall (e.g., double wall).

This concept could also be extended to non-capsule delivery systems. For example, materials with a vascular structure containing a solution of the active compound as above are envisioned to function similarly. In this case, mechanical damage of the material would rupture the vasculature in the region of damage causing release of the fluid and aggregation of the active component from solution, thus inducing a fluorescence response.

A Robust Damage-Reporting Strategy Enabled by Aggregation-Induced Emission

Figures 2A, 2B, 2C, 2D:
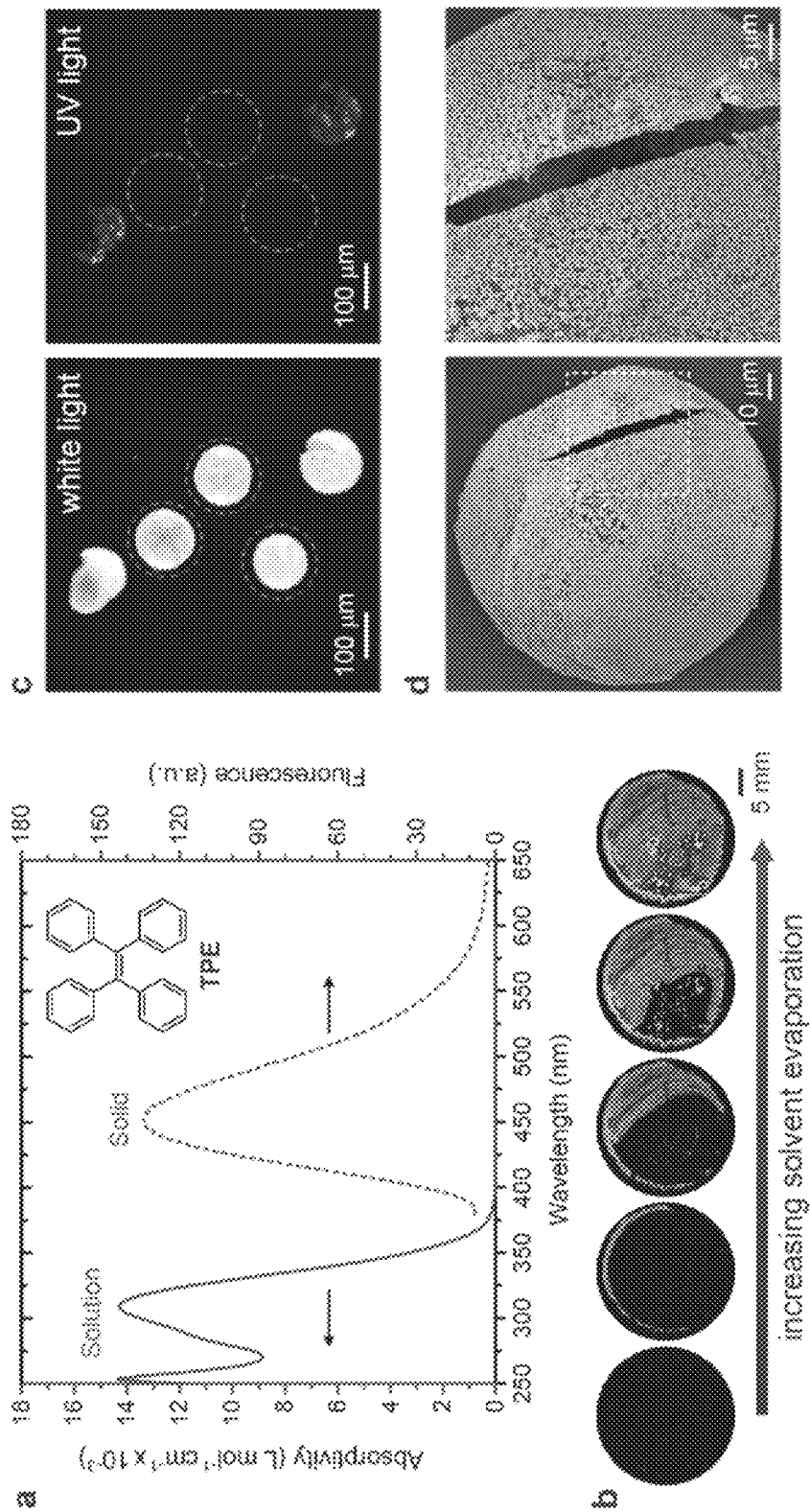
FIG. 2A-2D. Characterization of TPE fluorescence. (a) UV-vis absorption ($6.6 \times 10^{-5}$ M in hexyl acetate) and solid-state fluorescence emission spectra of TPE ($\lambda_{ex}$=365 nm). (b) Photographs of a TPE solution under illumination with UV light demonstrating the development of fluorescence upon solvent evaporation. (c) Stereomicrographs of TPE microcapsules under illumination with white light and UV light demonstrating damage-induced fluorescence. Intact microcapsules are undetectable under UV light, while ruptured microcapsules are fluorescent. The locations of intact microcapsules are outlined as a guide (dashed circles). (d) SEM images of a ruptured TPE microcapsule showing formation of TPE crystals on the shell wall.
Figures 6A, 6B:
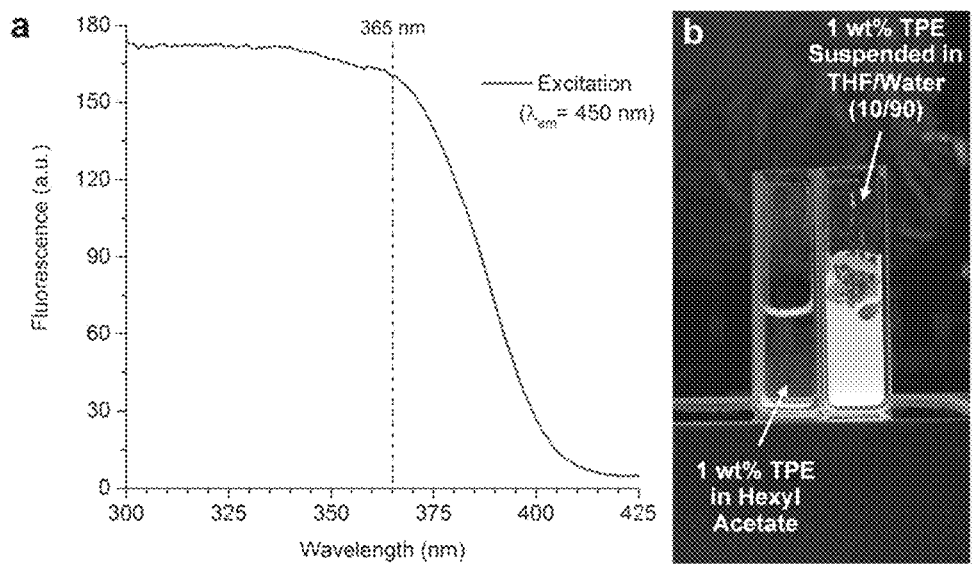
FIG. 6A-6B. (a) Fluorescence excitation spectrum of solid TPE cast from solution onto a glass substrate. Fluorescence emission was monitored at 450 nm. The wavelength corresponding to ordinary long-wave UV lamps (365 nm) is labeled with a dotted line as a visual guide. (b) Comparison of the fluorescence properties of TPE in solution versus in an aggregated form. The cuvette on the left contains a 1 wt % solution of TPE dissolved in hexyl acetate and is non-emissive when illuminated with 365 nm UV light. In contrast, a 1 wt % suspension of TPE in a water/THF mixture (90:10) exhibits bright blue fluorescence.

To demonstrate this concept, we investigated the commercially available AIE luminogen 1,1,2,2-tetraphenylethylene (TPE). Hexyl acetate was chosen as a solvent due to its suitability for microcapsule preparation, moderate boiling point (~170° C.), and contemporary use in industrial paint formulations. When TPE is dissolved in hexyl acetate, the solution is colorless and exhibits an absorption maximum at 310 nm (FIG. 2*a*). The solution is non-emissive under illumination with UV light, but a brilliant blue fluorescence with an emission maximum at 450 nm is observed from the solid residue formed upon solvent evaporation (FIG. 2*b*). The fluorescence excitation spectrum of solid TPE reveals relatively uniform emission intensity at excitation wavelengths between 300 and 370 nm, varying less than 10% over this range (FIG. 6). This expedient feature facilitates the use of ordinary UV light sources for visualization of the damage-induced fluorescence signal.

Figures 7A, 7B:
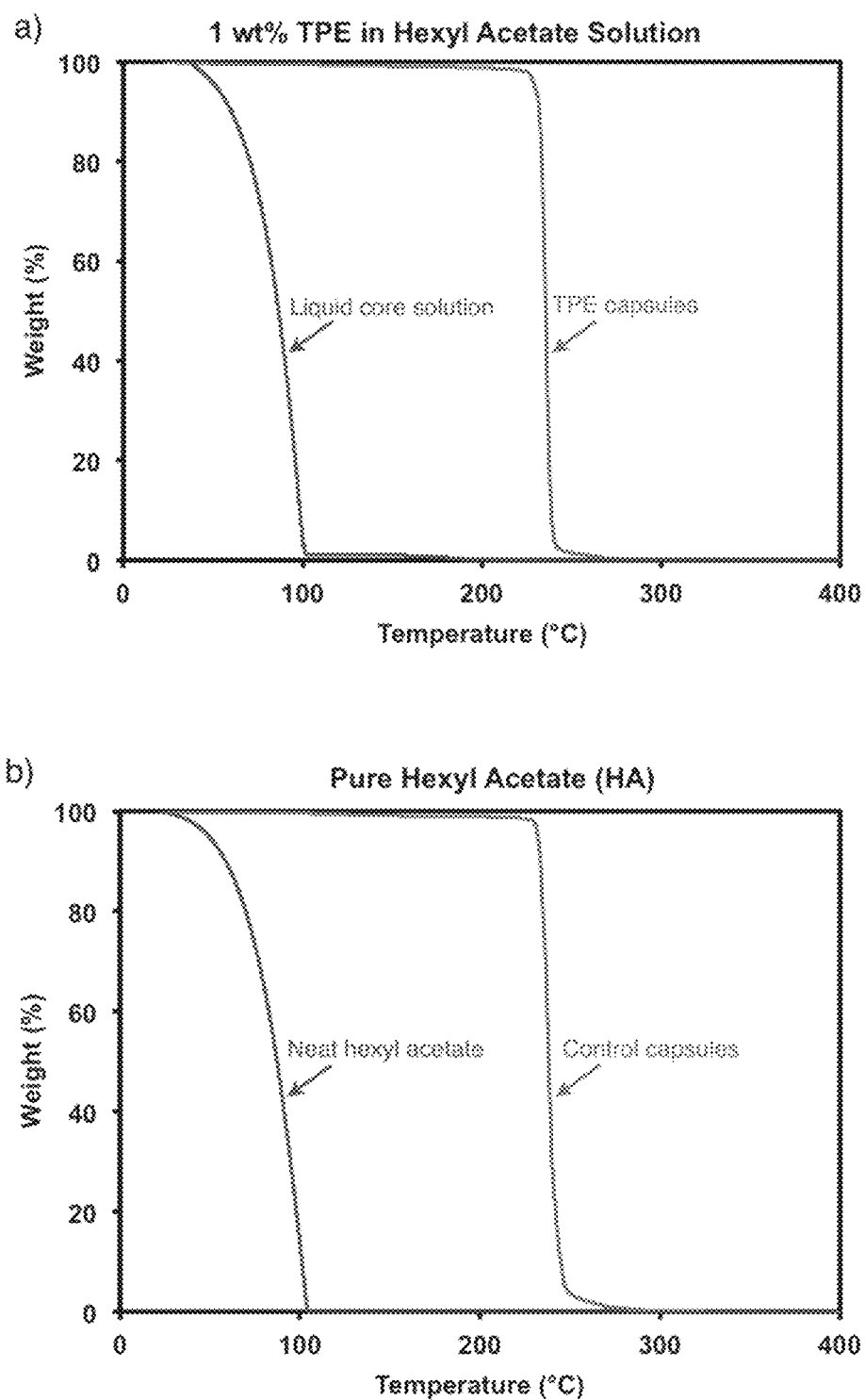
FIG. 7A-7B. Thermogravimetric analysis of (a) TPE microcapsules containing 1 wt % TPE in hexyl acetate in the core, and (b) control microcapsules containing only hexyl acetate demonstrates significantly enhanced thermal stability up to 220° C. compared to the unencapsulated core solutions (left line in each graph).
Figures 8A, 8B:
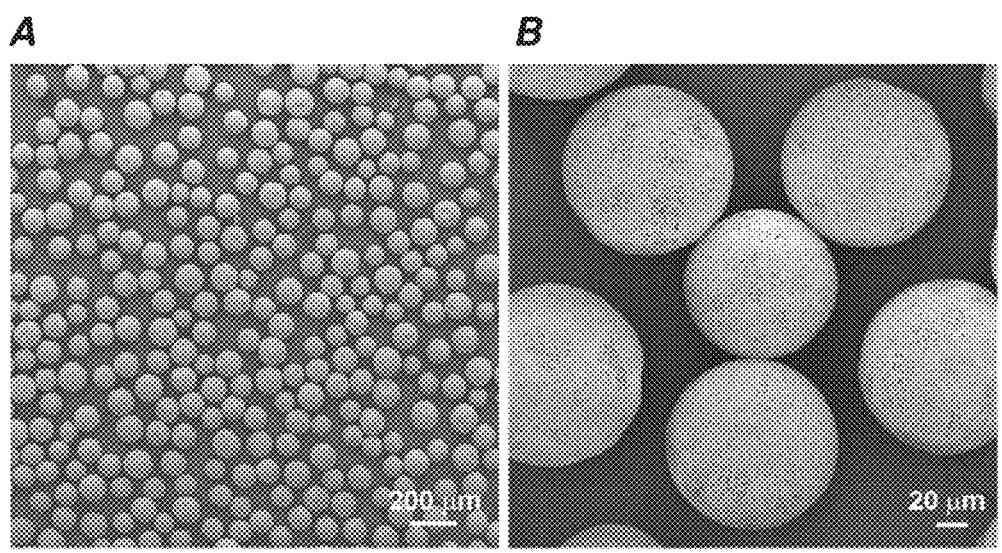
FIG. 8A-8B. SEM images of TPE microcapsules with diameter of 112±10 μm.

Core-shell microcapsules containing a 1 wt % (8.7 mg mL-1, 26 mM) solution of TPE in hexyl acetate were prepared using a well established in situ emulsification condensation polymerization method. The TPE microcapsules studied were 112±10 μm in diameter and exhibited excellent thermal stability up to 220° C. as demonstrated by thermogravimetric analysis (FIG. 7). SEM images of the microcapsules show that the majority were spherical in shape and remained intact after processing (FIG. 8). The thickness of the shell walls was approximately 300 nm based on analysis of SEM images of ruptured microcapsules. The TPE microcapsules are colorless due to the core material being completely transparent to all visible wavelengths of light, which is desirable for applications where the overall appearance of a material is potentially affected by the inclusion of additives. The fluorescence properties of TPE in solution were also maintained in the microcapsules, which were non-fluorescent under illumination with UV light, suggesting minimal background signal from the intact microcapsules when embedded in polymeric materials. The microcapsules remained non-emissive upon storage in ambient conditions for more than six months, which indicates the high stability of the TPE solutions contained in their core.

Figures 9A, 9B, 9C, 9D:
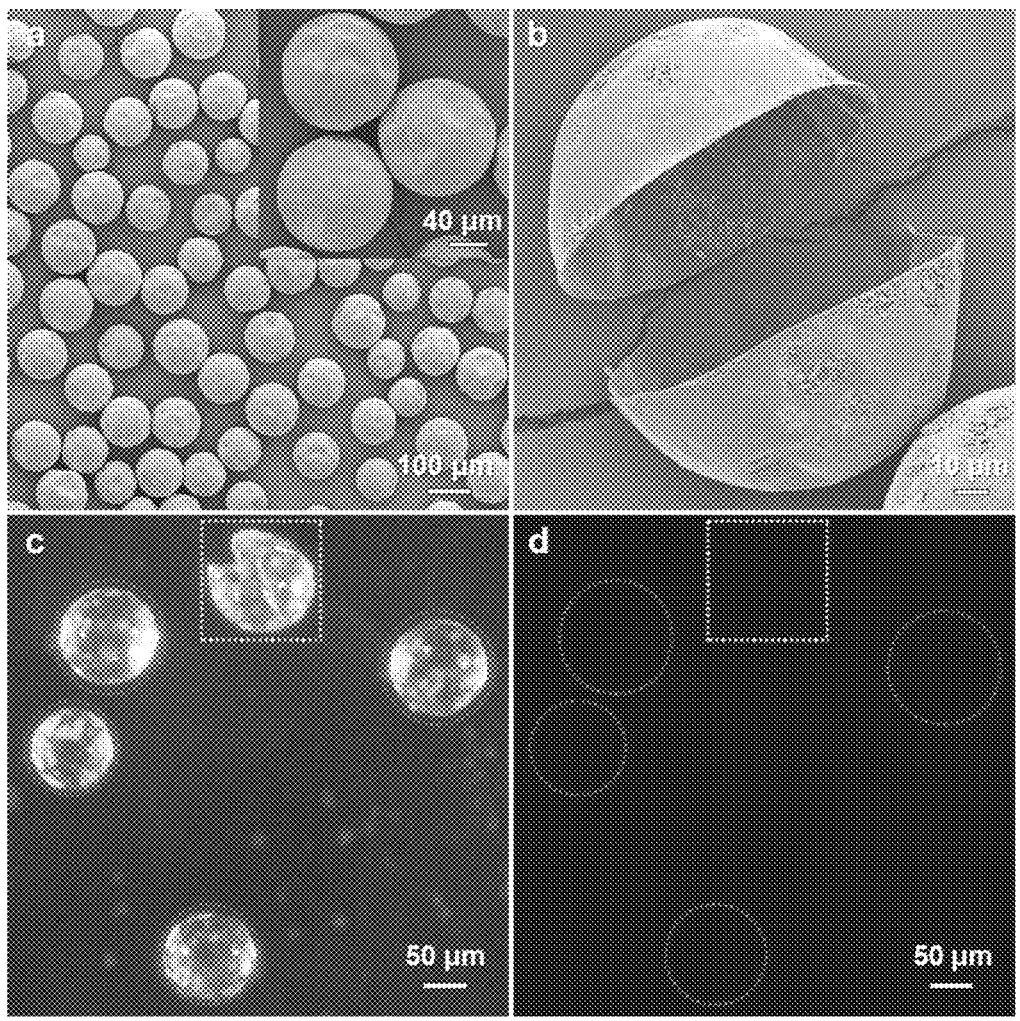
FIG. 9A-9D. SEM images of (a) intact and (b) ruptured control microcapsules containing only hexyl acetate in the core. Micrographs of control microcapsules under (c) white light and (d) UV light irradiation. Under UV light, both the intact (dashed circles) and ruptured microcapsules (white dashed square) are undetectable, demonstrating that TPE is responsible for the fluorescence indication in the TPE microcapsules.

The potential for TPE microcapsules to enable visual indication of mechanical damage was first evaluated by optical microscopy of both intact and ruptured microcapsules under illumination with white light and UV light (FIG. 2c and FIG. 17). TPE microcapsules were spread on a glass substrate and a portion of them was damaged using a razor blade. Under illumination with white light, regions where intact and ruptured microcapsules coexisted were clearly observed, facilitating investigation of the fluorescence properties of intact versus ruptured microcapsules at the single microcapsule level. Under illumination with UV light, microcapsules that were damaged (as observed under white light) exhibited distinct blue fluorescence while the intact microcapsules were undetectable. As a control, microcapsules containing only hexyl acetate in the core were also prepared and evaluated similarly. As expected, no fluorescence was detected from intact or ruptured control microcapsules, demonstrating that the TPE luminogen was responsible for the observed fluorescence response (FIG. 9). Additionally, SEM images of ruptured TPE microcapsules revealed crystalline deposits on the surface of the capsule shell which were absent in images of the ruptured control microcapsules (FIG. 2d).

Figures 3A, 3B, 3C, 3D, 3E, 3F:
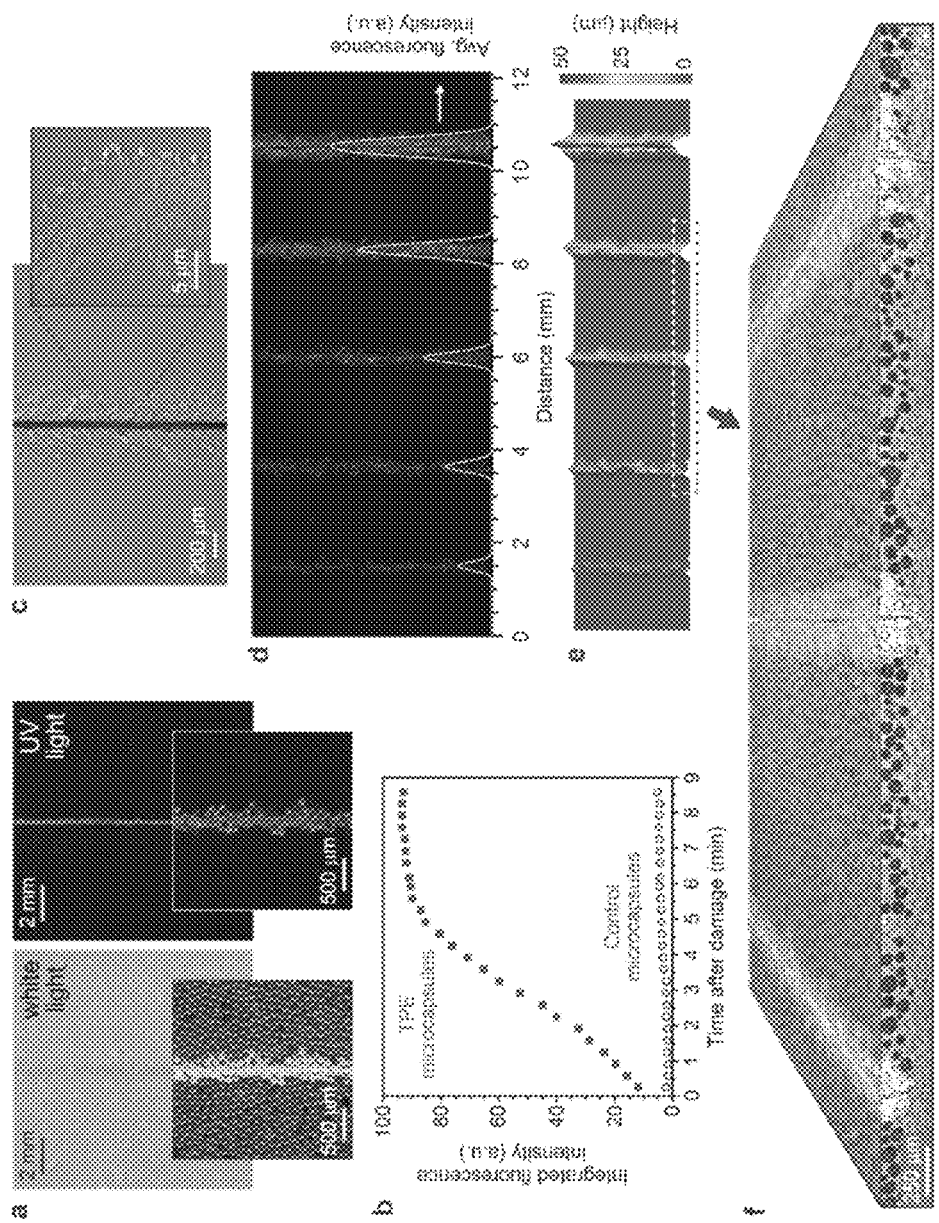
FIG. 3A-3F. Evaluation of damage detection performance in transparent epoxy coatings. (a) Photographs of an epoxy coating containing 10 wt % TPE microcapsules under illumination with white light and UV light after being scratched with a razor blade. Insets show stereomicrographs of the coating under similar illumination. (b) Time-dependent fluorescence microscopy measurements illustrating rapid development of a fluorescence signal after damage. A control coating incorporating microcapsules with only hexyl acetate in the core exhibits negligible change in fluorescence after damage. (c) SEM images illustrating solid TPE deposits in the shear region adjacent to the primary scratch damage. (d-f) Characterization of an epoxy coating containing 10 wt % TPE microcapsules with damage of varying size (average scratch depths from left to right: 94, 140, 171, 222, and 376 μm): fluorescence micrograph and overlaid fluorescence intensity profile (d), surface topology from profilometry (e), and magnified view of a 3D micro-CT reconstruction (f). Profilometry does not sufficiently resolve the scratch from the adjacent sheared region. In (f), intact microcapsules are rendered as black; ruptured microcapsules and damaged areas of the surface are white; the epoxy polymer matrix is shaded grey.
Figures 10A, 10B:
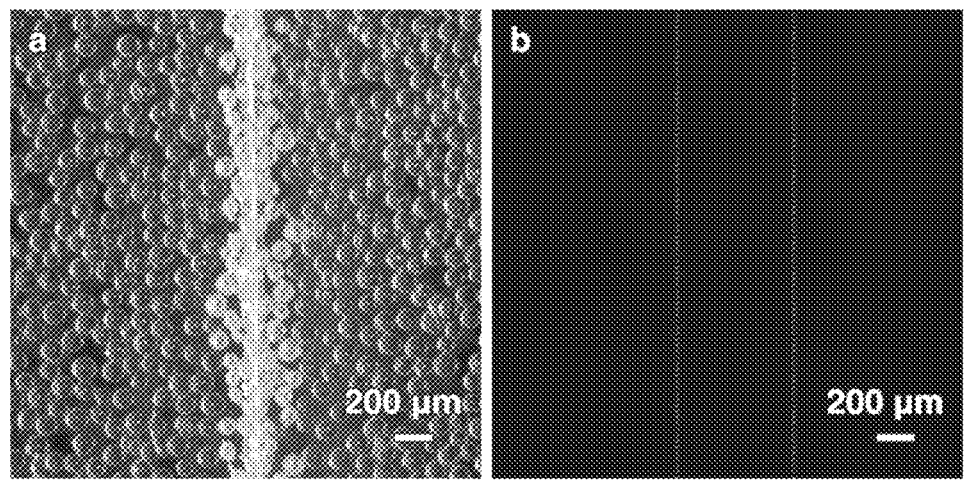
FIG. 10A-10B. Micrographs of an epoxy coating incorporating 10 wt % control microcapsules after being scratched with a razor blade under (a) white light and (b) UV light. No fluorescence signal is observed under UV light from the damaged coating. As a visual guide, the location of damage is indicated by the area inside of the dotted horizontal lines.

Transparent epoxy coatings incorporating 10 wt % TPE microcapsules were prepared to investigate autonomous damage indication capabilities for self-reporting engineering thermoset materials. Cured films were scratched with a razor blade and evaluated under white light and UV light sources (FIG. 3a and FIG. 18). Photographs of the scratched coating highlight the significant enhancement in visual identification of the damaged area under exposure to UV light, while higher magnification stereomicrographs demonstrate localization of the fluorescence response to individually ruptured microcapsules. Critically, areas outside of the damaged region remained completely non-emissive, providing excellent contrast between the damaged and intact regions of the coating. Moreover, the fluorescence signal developed rapidly after mechanical damage and was detectable almost immediately under UV light. Time-dependent fluorescence microscopy measurements demonstrated that maximum fluorescence intensity was reached after approximately 5 minutes in ambient conditions (FIG. 3b and FIG. 18). Analogous coatings prepared with control microcapsules were evaluated in an identical fashion with no changes in fluorescence observed after damage (FIG. 10).

Figures 11A, 11B:
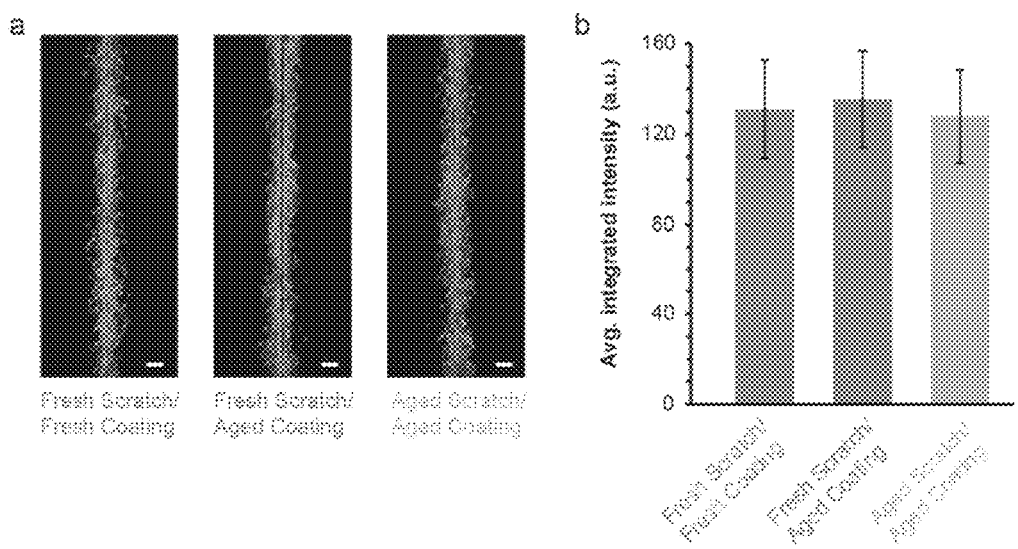
FIG. 11A-11B. Stability of damage indication performance. (a) Fluorescence micrographs of epoxy coatings containing 10 wt % TPE microcapsules at various time increments (scale bars, 250 μm). (b) The fluorescence response was quantified for a freshly prepared and scratched coating, a coating prepared and damaged 44 days previously (stored in ambient conditions), and the same aged coating that was scratched immediately prior to analysis, with each demonstrating equivalent indication.
Figure 12A:
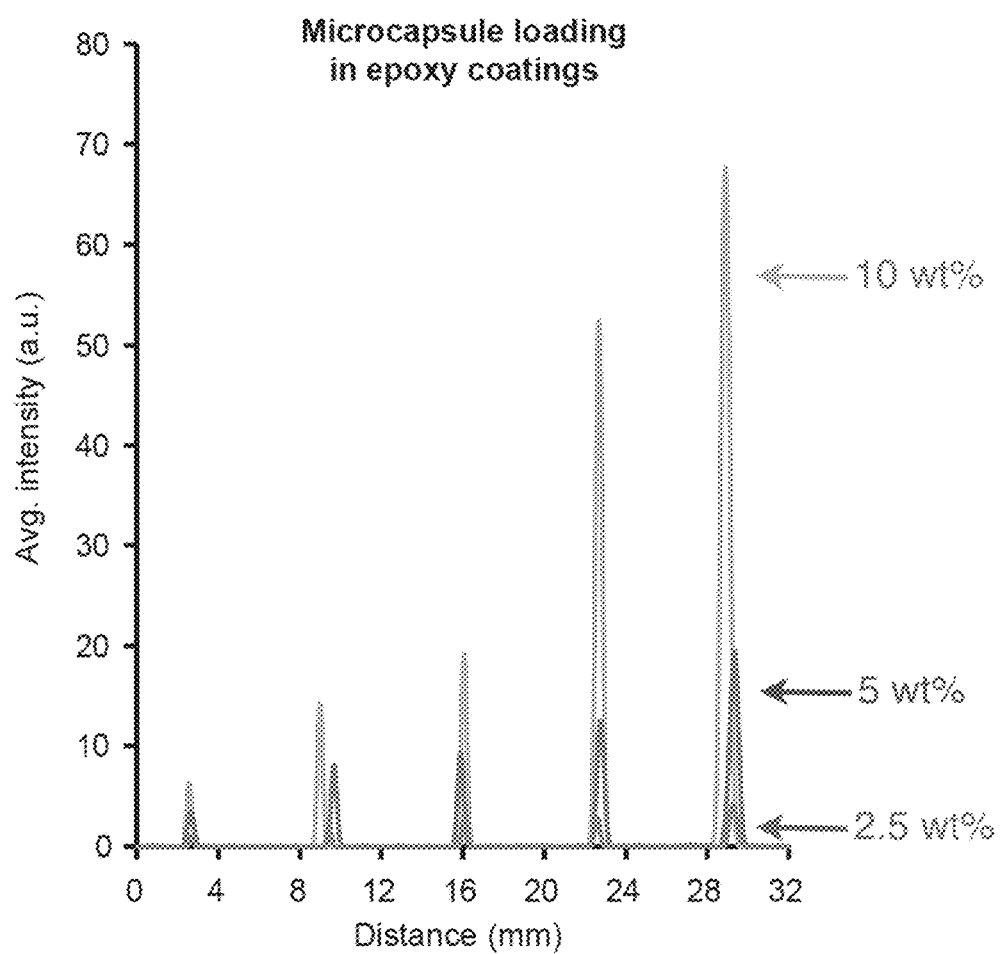
FIG. 12A and FIG. 12B. Effect of TPE concentration and microcapsule loading on damage indication performance in epoxy coatings. Coatings were scratched and then analyzed using fluorescence microscopy. (a) Fluorescence intensity profiles for epoxy coatings containing 2.5, 5, or 10 wt % TPE microcapsules (core concentration of 1 wt % TPE in hexyl acetate) with various scratch depths. Average scratch depth from left to right: 94, 140, 171, 222, and 376 μm.
Figure 12B:
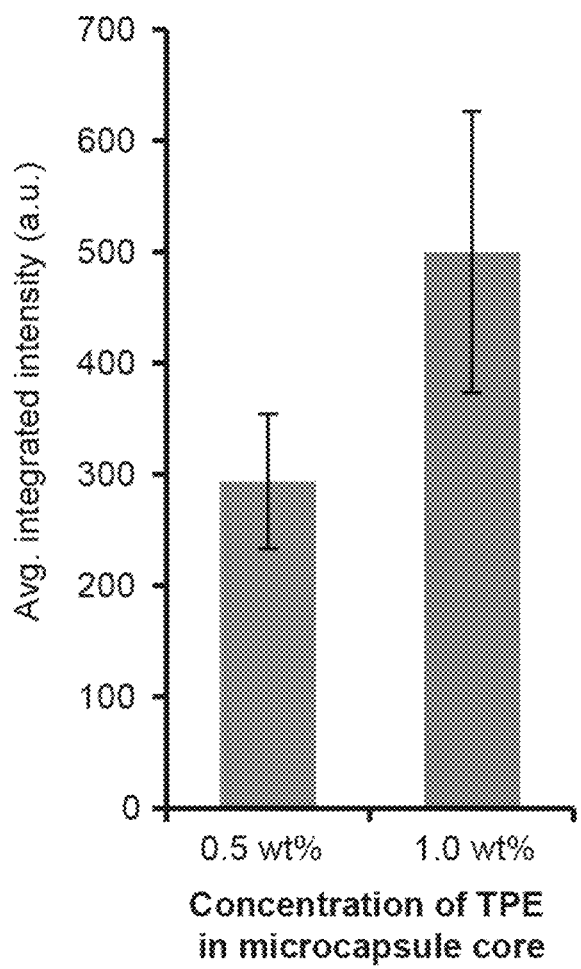

Epoxy coatings containing TPE microcapsules also demonstrated persistent damage indication capabilities. Scratched coatings stored for over one month in ambient conditions displayed equivalent fluorescence indication properties compared to freshly prepared and scratched coatings. Likewise, identical fluorescence behavior was observed for new scratches produced in aged coatings (FIG. 11). Damage indication was also uncompromised using microcapsules with a lower concentration of TPE in the core and lower microcapsule loadings; however, higher TPE concentration and incorporation of more microcapsules in coatings produced a more intense fluorescence response, as expected (FIG. 12).

Further studies were carried out to probe the relationship between fluorescence response and damage scale. SEM images of scratched epoxy coatings containing TPE microcapsules show solid deposits of TPE in sheared regions adjacent to the primary scratch damage (FIG. 3c).

Close inspection revealed evidence of ruptured microcapsules at the surface of the sheared region (FIG. 13). The high number of exposed, ruptured microcapsules in this region likely results in accelerated solvent evaporation and accounts for the intense and relatively diffuse fluorescence around the primary damage site. Furthermore, we reasoned that this feature would manifest in a fluorescence signal that is closely correlated with damage size. A series of scratches with varying depths (ca. 94-376 μm) were created in a similar epoxy specimen and the indication response was characterized using fluorescence microscopy (FIG. 3d). The area of the fluorescent region and the average intensity increased proportionately with cutting depth. Analysis of the surface topology of the specimen using profilometry confirmed that the area of the fluorescence signal was strongly correlated with the physically damaged area, which included significant shearing adjacent to the primary scratch (FIG. 3e); however, profilometry was unable to fully resolve these damage features. The relationship between mechanical damage and fluorescence response was further confirmed by characterizing the internal structure of the specimen using X-ray computed microtomography (micro-CT), which was able to differentiate between intact and ruptured microcapsules within the material and identify their location relative to matrix damage (FIG. 3f).

Figures 4A, 4B, 4C:
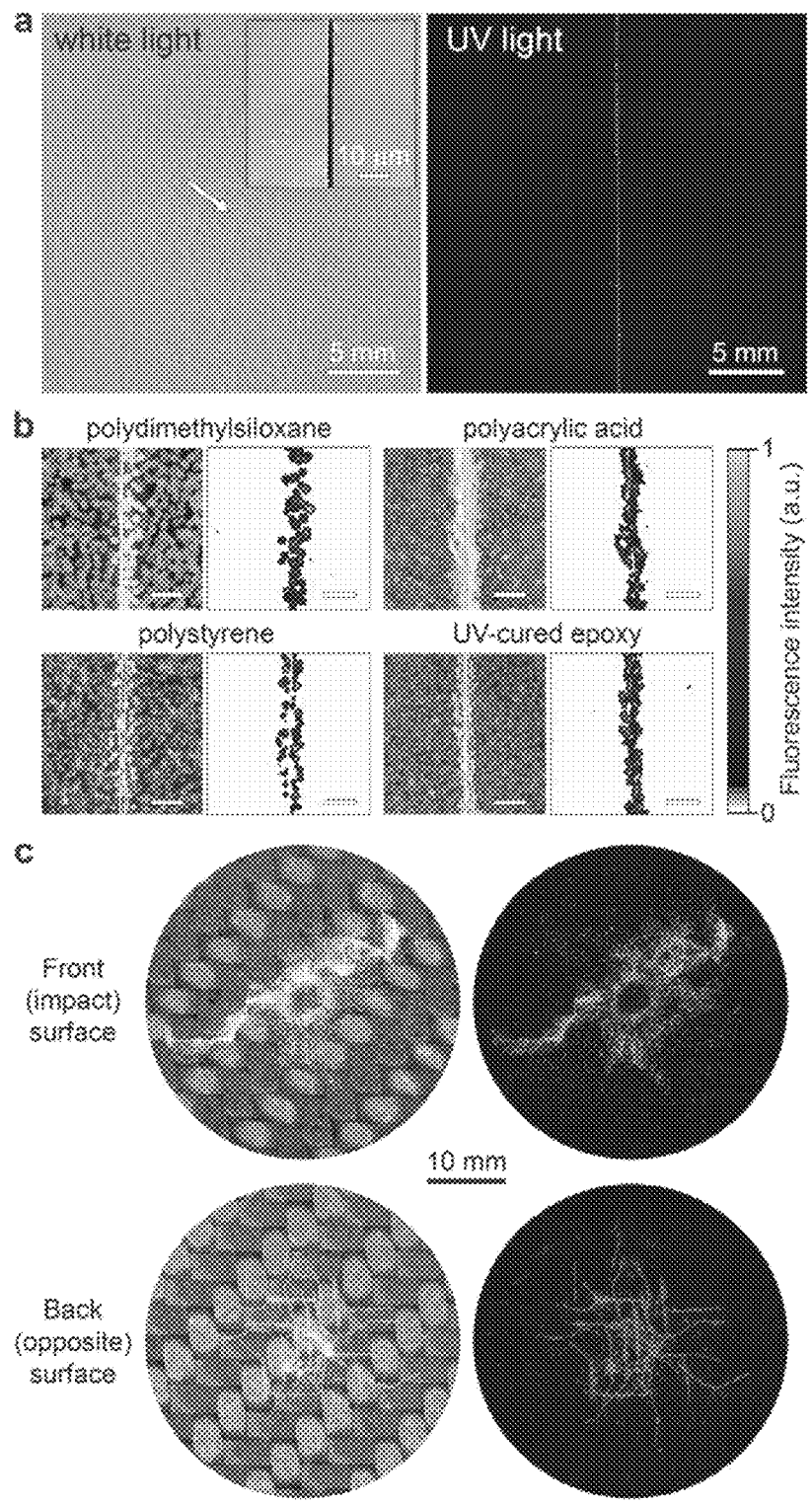
FIG. 4A-4C. Damage detection in a variety of materials and different damage modes. (a) Photographs of polyurethane coatings containing 10 wt % TPE microcapsules under illumination with white light and UV light after being scratched with a razor blade. Inset shows an SEM image of the scratch. (b) Stereomicrographs and corresponding fluorescence intensity maps of a variety of coating materials containing 10 wt % TPE microcapsules after being scratched with a razor blade (scale bars, 500 μm). (c) Photographs under white light and UV light of carbon fiber reinforced composite panels with an epoxy coating containing 10 wt % TPE microcapsules after impact.
Figure 5:
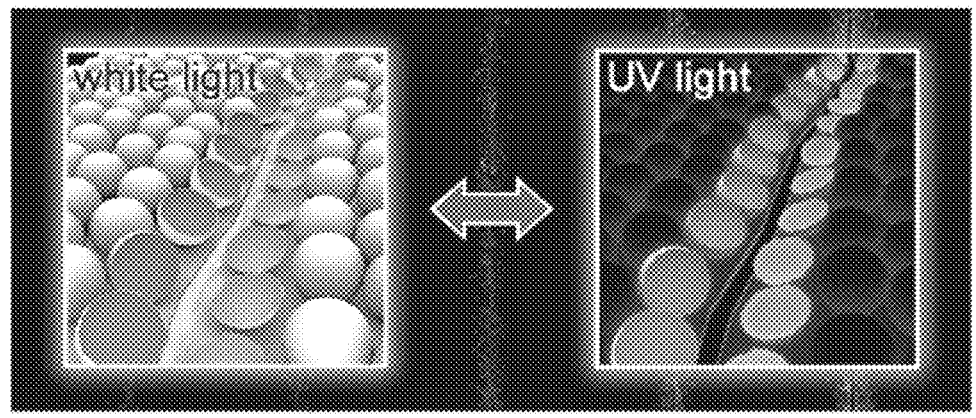
FIG. 5. Illustration of intact and ruptured TPE microcapsules, both visible under illumination with white light. Under UV light, the ruptured microcapsules appear fluorescent after being ruptured in contrast to the unruptured microcapsules.

To demonstrate the versatility of this method, we also investigated damage detection performance in a variety of different materials and different damage modes. Polyurethane coatings incorporating 10 wt % TPE microcapsules were prepared and examined under white light and UV light after being scratched with a razor blade (FIG. 4a and FIG. 15). Under ambient white lighting, the damage to the coating was nearly undetectable; however, under illumination with a handheld 365 nm UV lamp, the scratch was clearly visible, exhibiting a bright blue fluorescence signal. Similar to the epoxy coatings, intense fluorescence from the region of damage was detected rapidly after scratching the coating. SEM analysis revealed that the scratch was <2 μm wide, which is beyond the putative limit of unaided visual detection. Similar damage to coatings containing control microcapsules was undetectable (FIG. 14). Scratch damage was also clearly indicated in a variety of other polymeric coatings prepared using diverse fabrication techniques (FIG. 4b).

TPE microcapsules provided excellent detection performance in polydimethylsiloxane, UV-cured epoxy, polyacrylic acid cast from water, and polystyrene cast from toluene. The effectiveness of damage indication in these materials also highlights advantages of this approach over color changing strategies, which are typically limited to polymer matrices with minimal coloration to provide sufficient contrast. Additionally, indicating performance is maintained in materials utilizing diverse chemistries and curing conditions including prolonged exposure to intense UV irradiation. Finally, the ability to enhance damage visibility in carbon fiber reinforced composites was investigated, where barely visible impact damage is accompanied by severe deterioration in structural integrity. Composite specimens with an epoxy coating incorporating 10 wt % TPE microcapsules were subjected to a variety of impact tests and the resulting damage, including microcracks, was clearly discernible under UV light (FIG. 4c and FIG. 16). These experiments further illustrate the versatility of this technology and highlight the unique efficacy of this self-reporting system for enhancing the visual identification of damage in different materials systems.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Materials and General Methods

Polyurethane prepolymer (PU, Desmodur L 75) was obtained from Bayer MaterialScience. Ethylene maleic anhydride copolymer (EMA, Zemac-400, average molecular weight of 400,000 g/mol) was obtained from Vertellus (Indianapolis, Ind.). EPON epoxy resin 813 (74% diglycidyl ether of bisphenol-A and 26% o-cresyl glycidyl ether) and curing agent EPIKURE 3233 (polyoxypropylene triamine) were obtained from Miller-Stephenson (Houston, Tex.). Polyurethane coatings were prepared using a two-part acrylic polyurethane (Interthane 990, International Paint). Polydimethylsiloxane (PDMS) coatings were prepared using a two-part Sylgard 184 Silicone Elastomer (Dow Corning). Irgacure 250 photoinitiator (BASF) was used for the cationic polymerization of EPON resin 813 to prepare UV-cured epoxy coatings. Polystyrene (average molecular weight of 280,000 g/mol), polyacrylic acid (35 wt % in water, average molecular weight of 100,000 g/mol), 1,1,2,2-tetraphenylethylene, hexyl acetate (99%), urea, ammonium chloride, resorcinol, 1-octanol, formaldehyde solution (37 wt % in $H_2O$), sodium chloride (NaOH), and all of other chemicals were obtained from Sigma-Aldrich and used as received. Carbon fiber reinforced composites (404-11-Plate-Twill, 0.115 inches thick) were obtained from Rock West Composites and cut into 2 inch squares using a diamond saw.

UV-vis absorption spectra were measured from solutions of TPE in hexyl acetate (Shimadzu UV-2401PC spectrometer) with concentrations ranging from 66 μM to 26 mM. Fluorescence spectra of TPE were recorded from the solid deposited on a glass slide after evaporation of an ethyl acetate solution (Horiba FluoroMax-4). Thermal behavior of microcapsules was characterized by thermogravimetric analysis (TA Instrument Q50) with a heating rate of 10° C. $min^{-1}$ under nitrogen.

The core-shell structure and shell-wall thickness were obtained by imaging microcapsules that were mechanically ruptured with a razor blade or needle tip. Indication performance in smart coatings was assessed by imaging damaged specimens under both white light and UV light, using fluorescence light microscopy and stereomicroscopy.

Preparation of Microcapsules

Microcapsules were generally prepared according to a previously described encapsulation method (Caruso et. al., ACS Appl. Mater. Interfaces 2010, 2, 1195) using either 1 wt % TPE in hexyl acetate or neat hexyl acetate as the core solution. Polyurethane/poly(urea-formaldehyde) double-shell-wall microcapsules containing a hexyl acetate solution of TPE were prepared using a single batch process. Briefly, 0.83 g of urea, 83 mg of ammonium chloride, 83 mg of resorcinol, and two drops of 1-octanol were combined with 42 mL of a 0.5 wt % EMA aqueous solution. Under continuous mechanical agitation at 800 rpm, the core solution consisting of 174 mg TPE, 20 mL hexyl acetate, and 670 mg PU was slowly added to the aqueous mixture and allowed to emulsify for 10 min. Afterward, 2.1 g of formaldehyde (37% in water) was introduced and the reaction temperature was increased at a rate of 1° C./min to 55° C., and then maintained for 4 h. The prepared microcapsules were filtered, gently rinsed with deionized water to remove excess surfactant, dried, and sieved to isolate a certain size range. Microcapsules with a diameter of 112±10 μm were used for damage indication studies. Control microcapsules (diameter of 112±13 μm) were prepared using an identical procedure, emitting TPE from the core solution. Note that heating was required to dissolve TPE in hexyl acetate and produce optically clear solutions. Under ambient conditions, bulk solutions with TPE concentrations ≥0.9 wt % (24 mM) exhibited some precipitation after prolonged time; however, no evidence of aggregation or precipitation was observed for encapsulated solutions (1 wt % TPE) or bulk solutions with concentrations ≤0.82 wt % (21 mM) over a period of several months.

Fabrication of Coatings

Epoxy coatings were prepared by mixing a stoichiometric ratio of EPON 813 epoxy resin and EPIKURE 3233 curing agent (weight ratio of 100:43) with microcapsules added into the mixture at various weight percentages. The well-mixed dispersions were coated on glass slides or carbon fiber reinforced polymer composite substrates using a micrometer controlled doctor blade and cured at 35° C. for 24 h. Polyurethane and polydimethylsiloxane coatings were prepared in a similar fashion. UV-cured epoxy coatings were prepared using 5 wt % photoinitiator (Irgacure 250) and cured for 4 h under a 365 nm UV lamp (25 W Cole-Parmer UV Transilluminator). Polystyrene coatings were prepared by mixing a 30 wt % solution of polystyrene in toluene with 10 wt % microcapsules (with respect to polystyrene) and drop casting the well-mixed dispersion onto glass slides. The coatings were allowed to dry at room temperature for approximately 24 h inside a loosely covered glass dish to control the rate of solvent evaporation. Polyacrylic acid coatings were prepared similarly using a 35 wt % aqueous solution of polyacrylic acid.

The average thickness of coatings was controlled to be ~350 μm. Fluorescence microscopy was performed using an excitation source of 325-375 nm with an emission filter of 435-495 nm.

Characterization of Coatings

Coatings were examined using fluorescence light microscopy (Zeiss Observer Z1 inverted microscope with 350EX/460EM DAPI Chroma filter set 31000V2), stereomicroscopy (Zeiss SteREO Discovery V20 microscope), and scanning electron microscopy (Philips XL30 ESEM-FEG). Photographic images were acquired using a Canon EOS 7D digital camera equipped with a 425 nm longpass filter under ambient room lighting and illumination with a handheld UV source (OPTI-LUX 365 Series, Spectronics Corporation).

Reproducible scratches were created in epoxy coatings using a test panel scratcher (Corrocutter 639, Erichsen) with the scratch depth controlled by adjusting the load applied on the stylus. Scratch depths were measured using cross-sectional images obtained from microCT in five locations along the length of each scratch to provide an average depth and standard deviation as follows: 94±24 μm; 140 ±16 μm; 171±12 μm; 222±38 μm; 376±30 μm.

Image Analysis

Fluorescence micrographs were processed with Fiji (Schindelin et. al., Nat. Meth. 2012, 9, 676). Plots of fluoresecence intensity were generated in Origin Pro 2015 after applying a 3D smoothing function. Integrated intensities were measured by extracting individual scratches with equal area, dividing the images into at least 20 equal segments, and measuring the integrated density of each segment to provide an average and standard deviation. For the time-dependent fluorescence measurements, images were recorded at approximately 20 s intervals after scratching the coating with a razor blade. Images were cropped to the same pixel dimensions, background subtracted, and the integrated intensity was measured for the entire image containing the scratched region of the coating.

X-ray Computed Microtomography

MicroCT images were acquired on an Xradia BioCT (MicroXCT-400). 360 degree scans were obtained in rotation intervals of 0.4° using a 4× objective at 7 s exposure times with 40 keV (8 W, 200 μA). 3D image reconstructions were performed using TXM Reconstructor (v.8.1, Xradia) and visualized in 3D with TXM3Dviewer (v.1.1.6, Xradia). MicroCT images were post-processed in Amira (v.5.6.0, FEI).

Profilometry

Profilometry data was acquired on a KLA Tencor P-6 stylus profilometer with a 2 μm radius tip. The scan area was 10.5 mm×4 mm. The scanning, or x dimension was transverse to the scratch. Line scans were performed at a y spacing of 50 μm. The scan speed was 200 μm s$^{-1}$ and the sampling rate was 500 Hz. Profilometry data was processed in Matlab (Mathworks).

Impact Testing

Impact damage was created on coated carbon fiber reinforced composite panels using a drop-weight tower (Dynatup 8210) equipped with a 25 mm diameter hemispherical shaped striker. The drop height was 249 mm with corresponding impact energy of 10 J. The specimen was clamped into a square support fixture with a 38 mm diameter opening at the center of the panel.

Summary. Self-reporting materials with autonomous damage indication are achieved using core-shell microcapsules containing a dilute solution of an AIE luminogen. This system constitutes a simple and robust method that enables the visual detection of microscopic damage in a wide range of polymeric materials under illumination with an appropriate excitation light source, such as an ordinary long-wave UV light. Using microcapsules containing a solution of TPE in hexyl acetate, the fluorescence signal develops rapidly following mechanical damage to polymeric coatings and reaches maximum intensity in minutes. In contrast to alternative methods, this detection system is general and does not rely on any external or intermolecular interactions to elicit a response and provides outstanding contrast between intact and damaged regions with excellent sensitivity. We anticipate that the effectiveness of this technology coupled with its facile implementation will make it a useful tool for a variety of applications extending beyond damage detection.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. An autonomous self-indicating material comprising a plurality of microcapsules encapsulating a non-emissive solution, the solution comprising an aggregation-induced emission (AIE) luminogen and a solvent;
   wherein the material is configured to be impacted by a sufficient force to damage it, and one or more microcapsules are ruptured, the non-emissive solution is configured to be released from ruptured microcapsules, the luminogen aggregates at or near the point of rupture, and the aggregated luminogen is emissive to autonomically self-indicate a location where damage has occurred in the material.

2. The material of claim 1 wherein the material comprises a polymer.

3. The material of claim 2 wherein the polymer comprises an epoxy resin, a polyurethane, polydimethylsiloxane, polyacrylic acid, polystyrene, bisphenol A epoxy resin, bisphenol F epoxy resin, novolac epoxy resin, an aliphatic epoxy resin, a cycloaliphatic epoxy resin, a glycidylamine epoxy resin, a water-based epoxy resin, a bisphenol A diglycidyl ether (DGEBA) based resin, or a combination thereof.

4. The material of claim 1 wherein the microcapsules comprise about 1 weight percent to about 30 weight percent of the total weight of the material.

5. The material of claim 1 wherein the solvent comprises an (alkyl)acetate, an alcohol, an ether, an alkane, a ketone, a nitrile, water, an aromatic hydrocarbon, a protic solvent, an aprotic solvent, or a combination thereof.

6. The material of claim 1 wherein the solution comprises the luminogen at about 0.05 weight percent to about 20 weight percent.

7. The material of claim 1 wherein the microcapsules have a thermal stability up to about 400° C.

8. The material of claim 1 wherein the diameter of the microcapsules is about 200 nm to about 500 μm.

9. The material of claim 1 wherein the microcapsules have a shell-wall thickness of about 10 nm to about 50 μm.

10. The material of claim 1 wherein the microcapsules comprise a double-walled mixture of polyurethane and poly(ureaformaldehyde), or the microcapsules comprise a single-wall of polyurethane or poly(ureaformaldehyde).

11. A substrate comprising a coating of the material of claim 1 wherein the substrate comprises steel, aluminum, iron, zinc, copper, titanium, carbon, silica, a ceramic, cellulose, glass, a fiber, a polymer, or a combination thereof.

12. The substrate of claim 11 wherein the thickness of the coating is about 5 μm to about 10 mm.

13. The material of claim 1 wherein the luminogen is 1,1,2,2-tetraphenylethylene (TPE), fluorescein, hexaphenylsilole (HPS), 10,10',11,11'-tetrahydro-5,5'-bidibenzo[a,d][7]

annulenylidene (THBA), 9-(diphenylmethylene)-9 H-fluorene (DPMF), or 9, 10-Bis(p-dimethylaminostyryl) anthracene.

14. An autonomous self-indicating composite material comprising:
    a vessel containing a non-emissive solution comprising an aggregation-induced emission (AIE) luminogen and a solvent;
    a mixture of a polymer and a plurality of vessels; and
    a substrate comprising a coating of the mixture;
    wherein the composite material is configured to be impacted by a sufficient force to damage it, and one or more vessels are ruptured, the non-emissive solution is configured to be released from each ruptured vessel, the luminogen aggregates at or near the point of rupture, and the aggregated luminogen is emissive to autonomically self-indicate a location where damage has occurred in the composite material.

15. The composite material of claim 14 wherein the vessel is a substantially spheroid microcapsule encapsulating the solution, or the vessel has a microvascular structure comprising a hollow network of channels or fibers or capillaries, or a combination thereof, wherein the vessel is partially or substantially filled with the solution.

16. A method for preparing the autonomous self-indicating material of claim 1 comprising:
    a) dissolving a luminogen in a solvent to form a non-emissive solution;
    b) preparing microcapsules and encapsulating the non-emissive solution into the microcapsules;
    c) mixing an epoxy resin or a polyurethane with the microcapsules to form the material; and;
    d) coating the material onto a substrate.

17. A method for detecting damage to an autonomous self-indicating material, the method comprising:
    a) irradiating an autonomous self-indicating material with ultraviolet light, wherein the material comprises a plurality of microcapsules encapsulating a non-emissive solution comprising an aggregation-induced emission (AIE) luminogen and a solvent;
    wherein when the material is impacted by a sufficient force to damage it, one or more microcapsules are ruptured, the non-emissive solution is released from ruptured microcapsules, the luminogen aggregates at or near the point of rupture, and the aggregated luminogen is emissive to autonomically self-indicate a location where damage has occurred in the material; and
    b) determining if a fluorescent signal is emitted by the luminogen;
    wherein the absence of the fluorescent signal indicates that there is no damage to the material and the presence of the fluorescent signal autonomically self-indicates the location of damage to the material.

18. The method of claim 17 wherein composite is irradiated with ultraviolet light of about 365 nm.

19. The method of claim 17 wherein when the microcapsules are ruptured, the solvent is substantially removed from the point of rupture by evaporation, diffusion, absorption, adsorption, or a combination thereof.

20. The method of claim 19 wherein the solvent is substantially removed in less than about 24 hours.

21. A method for detecting damage to the autonomous self-indicating material of claim 1 comprising:
    a) irradiating the material with ultraviolet light; and
    b) determining if a fluorescent signal is emitted by the organic luminogen;
    wherein the absence of the fluorescent signal indicates that there is no damage to the material and the presence of the fluorescent signal autonomically self-indicates the location of damage to the material.

* * * * *